(12) United States Patent
Surti et al.

(10) Patent No.: US 11,931,227 B2
(45) Date of Patent: Mar. 19, 2024

(54) BIMODAL TREATMENT METHODS AND COMPOSITIONS FOR GASTROINTESTINAL LESIONS WITH ACTIVE BLEEDING

(71) Applicant: Cook Medical Technologies LLC, Bloomington, IN (US)

(72) Inventors: Vihar C. Surti, Winston-Salem, NC (US); Shaun D. Gittard, Winston-Salem, NC (US); John C. Sigmon, Jr., Winston-Salem, NC (US); Gregory Hardy, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 184 days.

(21) Appl. No.: 15/581,876

(22) Filed: Apr. 28, 2017

(65) Prior Publication Data
US 2017/0232141 A1    Aug. 17, 2017

Related U.S. Application Data

(63) Continuation-in-part of application No. 14/209,718, filed on Mar. 13, 2014, now abandoned, and a continuation-in-part of application No. 14/044,040, filed on Oct. 2, 2013, now Pat. No. 9,867,931.

(60) Provisional application No. 61/793,586, filed on Mar. 15, 2013.

(51) Int. Cl.
| | |
|---|---|
| A61F 13/04 | (2006.01) |
| A61F 13/00 | (2006.01) |
| A61F 13/02 | (2006.01) |
| A61L 15/22 | (2006.01) |
| A61L 15/58 | (2006.01) |
| A61L 24/00 | (2006.01) |
| A61L 26/00 | (2006.01) |

(52) U.S. Cl.
CPC ........ *A61F 13/04* (2013.01); *A61F 13/00063* (2013.01); *A61F 13/023* (2013.01); *A61F 13/0253* (2013.01); *A61L 15/225* (2013.01); *A61L 15/58* (2013.01); *A61L 24/001* (2013.01); *A61L 26/0061* (2013.01); *A61L 2300/418* (2013.01); *A61L 2400/04* (2013.01); *A61L 2400/06* (2013.01)

(58) Field of Classification Search
None
See application file for complete search history.

(56) References Cited

U.S. PATENT DOCUMENTS

| | | |
|---|---|---|
| 39,678 A | 8/1863 | Russell |
| 170,182 A | 11/1875 | Molesworth |
| 442,785 A | 12/1890 | Schoettl |
| 460,458 A | 9/1891 | Bates |
| 471,865 A | 3/1892 | Howard |
| 533,489 A | 2/1895 | Ogram |
| 566,411 A | 8/1896 | Schoene |
| 576,437 A | 2/1897 | Elliot |
| 693,587 A | 2/1902 | Campbell |
| 775,985 A | 11/1904 | McKain |
| 881,238 A | 3/1908 | Hasbrouck |
| 904,149 A | 11/1908 | Rachmann |
| 938,648 A | 11/1909 | DeVilbiss |
| 1,022,601 A | 4/1912 | Rumberg et al. |
| 1,114,114 A | 10/1914 | Cochenour |
| 1,145,520 A | 7/1915 | Smith |
| 1,261,503 A | 4/1918 | Figgis |
| 1,357,452 A | 11/1920 | Hall |
| 1,466,119 A | 8/1923 | Claflin |
| 1,521,396 A | 12/1924 | Scott |
| 1,685,280 A | 9/1928 | Findley |
| 1,934,793 A | 11/1933 | Crain et al. |
| 2,004,402 A | 6/1935 | Conklin |
| 2,151,418 A | 3/1939 | Bolte |
| 2,223,611 A | 12/1940 | Gross |
| 2,307,986 A | 1/1943 | Bolte et al. |
| 2,390,313 A | 12/1945 | Macgill |
| 2,507,702 A | 5/1950 | Fields |
| 2,519,555 A | 8/1950 | Fields |
| 2,609,155 A | 9/1952 | Fosnaugh |
| 2,632,444 A | 3/1953 | Kas |

(Continued)

FOREIGN PATENT DOCUMENTS

| | | |
|---|---|---|
| CH | 15244 A | 9/1897 |
| CH | 257250 A | 3/1949 |

(Continued)

OTHER PUBLICATIONS

Japanese Reporting Letter, Final Decision for Rejection issued in Japanese Patent Application No. 2016-500548 dated Dec. 6, 2016 and English translation thereof.

(Continued)

*Primary Examiner* — Patricia Duffy
*Assistant Examiner* — Garen Gotfredson
(74) *Attorney, Agent, or Firm* — Crowell & Moring LLP (57) ABSTRACT

The present invention relates to a long-lasting medical product for protecting or treating a lesion in the gastrointestinal tract. The medical product includes a protective covering, wherein the medical product upon application at and about the site of the lesion adheres to the gastrointestinal tissue and is capable of remaining at and about the site of the lesion for a time sufficient to allow the lesion to heal or be treated.

15 Claims, 3 Drawing Sheets

(2 of 3 Drawing Sheet(s) Filed in Color)

(56) References Cited

U.S. PATENT DOCUMENTS

| | | |
|---|---|---|
| 2,805,013 A | 9/1957 | Cordis |
| 2,934,314 A | 4/1960 | Chambers et al. |
| 2,956,579 A | 10/1960 | Moore et al. |
| 3,016,895 A | 1/1962 | Sein et al. |
| 3,050,261 A | 8/1962 | Littlefield |
| 3,506,008 A | 4/1970 | Huck |
| 3,540,444 A | 11/1970 | Moreland |
| 3,572,335 A | 3/1971 | Robinson |
| 3,589,363 A | 6/1971 | Banko et al. |
| 3,599,866 A | 8/1971 | Bolton |
| 3,632,046 A | 1/1972 | Hengesbach |
| 3,647,143 A | 3/1972 | Gauthier et al. |
| 3,649,299 A | 3/1972 | Sholl |
| 3,667,465 A | 6/1972 | Voss |
| 3,710,400 A | 1/1973 | Sparks |
| 3,742,955 A | 7/1973 | Battista et al. |
| 3,744,493 A | 7/1973 | Booher et al. |
| 3,762,410 A | 10/1973 | Bindel |
| 3,788,315 A | 1/1974 | Laurens |
| 3,815,595 A | 6/1974 | Bar |
| 3,900,022 A | 8/1975 | Widran |
| 3,916,896 A | 11/1975 | Ballard |
| 4,017,007 A | 4/1977 | Riccio |
| 4,040,420 A | 8/1977 | Speer |
| 4,174,811 A | 11/1979 | Binder et al. |
| 4,184,258 A | 1/1980 | Barrington et al. |
| 4,204,539 A | 5/1980 | Van Brugge |
| 4,204,645 A | 5/1980 | Hopp |
| 4,210,140 A | 7/1980 | James et al. |
| 4,359,049 A | 11/1982 | Redl et al. |
| 4,373,519 A | 2/1983 | Errede et al. |
| 4,423,727 A | 1/1984 | Widran et al. |
| 4,427,650 A | 1/1984 | Stroetmann |
| 4,516,442 A | 5/1985 | Davis |
| 4,517,173 A | 5/1985 | Kizawa et al. |
| 4,534,345 A | 8/1985 | Wetterlin |
| 4,539,716 A | 9/1985 | Bell |
| 4,578,067 A | 3/1986 | Cruz, Jr. |
| 4,606,501 A | 8/1986 | Bate et al. |
| 4,620,847 A | 11/1986 | Shishov et al. |
| 4,631,055 A | 12/1986 | Redl et al. |
| 4,637,816 A | 1/1987 | Mann |
| H257 H | 4/1987 | Barditch et al. |
| 4,655,211 A | 4/1987 | Sakamoto et al. |
| 4,735,616 A | 4/1988 | Eibl et al. |
| 4,738,658 A | 4/1988 | Magro et al. |
| 4,738,740 A | 4/1988 | Pinchuk |
| 4,752,466 A | 6/1988 | Saferstein et al. |
| 4,771,077 A | 9/1988 | Reuter et al. |
| 4,790,819 A | 12/1988 | Li et al. |
| 4,798,606 A | 1/1989 | Pinchuk |
| 4,803,977 A | 2/1989 | Kremer, Jr. |
| 4,846,405 A | 7/1989 | Zimmermann |
| D303,139 S | 8/1989 | Morgan |
| 4,872,450 A | 10/1989 | Austad |
| 4,874,368 A | 10/1989 | Miller et al. |
| 4,890,612 A | 1/1990 | Kensey |
| 4,900,303 A | 2/1990 | Lemelson |
| 4,902,278 A | 2/1990 | Maget et al. |
| 4,902,281 A | 2/1990 | Avoy |
| 4,927,410 A | 5/1990 | Kovacs |
| 4,929,246 A | 5/1990 | Sinofsky |
| 4,941,874 A | 7/1990 | Sandow et al. |
| 4,941,880 A | 7/1990 | Burns |
| 4,945,050 A | 7/1990 | Sanford et al. |
| 4,946,870 A | 8/1990 | Partain, III et al. |
| 4,950,234 A | 8/1990 | Fujioka et al. |
| 4,969,874 A | 11/1990 | Michel et al. |
| 4,978,336 A | 12/1990 | Capozzi et al. |
| 4,994,028 A | 2/1991 | Leonard et al. |
| 5,009,637 A | 4/1991 | Newman et al. |
| 5,015,580 A | 5/1991 | Christou et al. |
| 5,021,059 A | 6/1991 | Kensey et al. |
| 5,053,000 A | 10/1991 | Booth et al. |
| 5,059,187 A | 10/1991 | Sperry et al. |
| 5,061,180 A | 10/1991 | Wiele |
| 5,063,025 A | 11/1991 | Ito |
| 5,064,413 A | 11/1991 | McKinnon et al. |
| 5,106,370 A | 4/1992 | Stewart |
| 5,116,315 A | 5/1992 | Capozzi et al. |
| 5,120,657 A | 6/1992 | McCabe et al. |
| 5,129,825 A | 7/1992 | Discko, Jr. |
| 5,129,882 A | 7/1992 | Weldon et al. |
| 5,133,701 A | 7/1992 | Han |
| 5,141,515 A | 8/1992 | Eberbach |
| 5,147,292 A | 9/1992 | Kullas et al. |
| 5,149,655 A | 9/1992 | McCabe et al. |
| 5,165,604 A | 11/1992 | Copp, Jr. |
| 5,176,642 A | 1/1993 | Clement |
| 5,179,022 A | 1/1993 | Sanford et al. |
| D333,000 S | 2/1993 | Good et al. |
| 5,204,253 A | 4/1993 | Sanford et al. |
| 5,219,328 A | 6/1993 | Morse et al. |
| 5,226,567 A | 7/1993 | Sansalone |
| 5,226,877 A | 7/1993 | Epstein |
| 5,260,066 A | 11/1993 | Wood et al. |
| 5,273,531 A | 12/1993 | Knoepfler |
| 5,292,309 A | 3/1994 | Van Tassel et al. |
| 5,310,407 A | 5/1994 | Casale |
| 5,312,333 A | 5/1994 | Churinetz et al. |
| 5,328,459 A | 7/1994 | Laghi |
| 5,391,183 A | 2/1995 | Janzen et al. |
| 5,392,992 A | 2/1995 | Farnsteiner et al. |
| 5,395,326 A | 3/1995 | Haber et al. |
| 5,405,607 A | 4/1995 | Epstein |
| 5,415,631 A | 5/1995 | Churinetz et al. |
| 5,429,278 A | 7/1995 | Sansalone |
| 5,445,612 A | 8/1995 | Terakura et al. |
| 5,447,499 A | 9/1995 | Allaire et al. |
| 5,469,994 A | 11/1995 | Reh et al. |
| 5,470,311 A | 11/1995 | Setterstrom et al. |
| 5,484,403 A | 1/1996 | Yaokum et al. |
| 5,503,623 A | 4/1996 | Tilton, Jr. |
| 5,520,658 A | 5/1996 | Holm |
| 5,538,162 A | 7/1996 | Reh et al. |
| 5,553,741 A | 9/1996 | Sancoff et al. |
| 5,558,646 A | 9/1996 | Roche |
| 5,582,596 A | 12/1996 | Fukunaga et al. |
| 5,584,807 A | 12/1996 | McCabe |
| 5,584,815 A | 12/1996 | Pawelka et al. |
| 5,601,603 A | 2/1997 | Illi |
| 5,605,541 A | 2/1997 | Holm |
| 5,612,050 A | 3/1997 | Rowe et al. |
| 5,665,067 A | 9/1997 | Linder et al. |
| 5,697,947 A | 12/1997 | Wolf et al. |
| 5,707,402 A | 1/1998 | Heim |
| 5,749,968 A | 5/1998 | Melanson et al. |
| 5,759,171 A | 6/1998 | Coelho |
| 5,773,033 A * | 6/1998 | Cochrum ............... A61K 35/16 424/530 |
| 5,788,625 A | 8/1998 | Plouhar et al. |
| 5,865,796 A | 2/1999 | McCabe |
| 5,873,530 A | 2/1999 | Chizinsky |
| 5,902,228 A | 5/1999 | Schulsinger et al. |
| 5,919,184 A | 7/1999 | Tilton, Jr. |
| 5,922,749 A | 7/1999 | Tyers et al. |
| 5,951,531 A * | 9/1999 | Ferdman ............... A61M 11/02 604/82 |
| 6,007,515 A | 12/1999 | Epstein et al. |
| 6,013,050 A | 1/2000 | Bellhouse et al. |
| 6,021,776 A | 2/2000 | Allred et al. |
| 6,027,471 A | 2/2000 | Fallon et al. |
| 6,059,749 A | 5/2000 | Marx |
| 6,077,217 A | 6/2000 | Love et al. |
| 6,117,150 A | 9/2000 | Pingleton et al. |
| 6,165,201 A | 12/2000 | Sawhney et al. |
| 6,348,502 B1 | 2/2002 | Gardiner et al. |
| 6,368,300 B1 | 4/2002 | Fallon et al. |
| 6,394,975 B1 | 5/2002 | Epstein |
| 6,395,307 B1 | 5/2002 | Banning et al. |
| 6,454,786 B1 | 9/2002 | Holm et al. |
| 6,461,325 B1 | 10/2002 | Delmotte et al. |
| 6,461,361 B1 | 10/2002 | Epstein |
| 6,478,754 B1 | 11/2002 | Babaev |

(56) References Cited

U.S. PATENT DOCUMENTS

| | | | |
|---|---|---|---|
| 6,537,246 B1 | 5/2003 | Unger et al. |
| 6,585,997 B2 | 7/2003 | Moro et al. |
| 6,610,026 B2 | 8/2003 | Cragg et al. |
| 6,641,800 B1 | 11/2003 | Mistry et al. |
| 6,689,108 B2 | 2/2004 | Lavi et al. |
| 6,716,190 B1 | 4/2004 | Glines et al. |
| 6,723,067 B2 | 4/2004 | Nielson |
| 6,811,550 B2 | 11/2004 | Holland et al. |
| 6,843,388 B1 | 1/2005 | Hollars |
| 6,863,660 B2 | 3/2005 | Marx |
| 6,939,324 B2 | 9/2005 | Gonnelli et al. |
| 7,101,862 B2 | 9/2006 | Chochrum et al. |
| 7,156,880 B2 | 1/2007 | Evans et al. |
| 7,291,133 B1 | 6/2007 | Kindler et al. |
| 7,303,759 B2 | 12/2007 | Mershon |
| 7,334,598 B1 | 2/2008 | Hollars |
| 7,514,248 B2 | 4/2009 | Gower et al. |
| 7,514,249 B2 | 4/2009 | Gower et al. |
| 7,534,449 B2 | 5/2009 | Saltzman et al. |
| 7,544,177 B2 | 6/2009 | Gertner |
| 7,544,348 B2 | 6/2009 | Jacob et al. |
| 7,544,496 B2 | 6/2009 | Gower et al. |
| 7,547,433 B2 | 6/2009 | Jacob et al. |
| 7,632,245 B1 | 12/2009 | Cowan et al. |
| 7,673,783 B2 | 3/2010 | Morgan et al. |
| 7,691,244 B2 | 4/2010 | Levitan et al. |
| 7,744,526 B2 | 6/2010 | McAlister et al. |
| 7,776,822 B2 | 8/2010 | Terman |
| 7,803,392 B2 | 9/2010 | Mumper et al. |
| 7,824,373 B2 | 11/2010 | Kim |
| 7,857,167 B1 | 12/2010 | Hollars |
| 7,943,169 B2 | 5/2011 | Domb et al. |
| 8,048,413 B2 | 11/2011 | Huguet et al. |
| 8,106,030 B2 | 1/2012 | Hardy et al. |
| 8,388,984 B2 | 3/2013 | Huguet et al. |
| 8,445,009 B2 | 5/2013 | MacPhee et al. |
| 8,529,939 B2 | 9/2013 | Masters et al. |
| 8,530,573 B2 | 9/2013 | Dershem |
| 8,658,198 B2 | 2/2014 | Pettersson |
| 8,663,192 B2 | 3/2014 | Hester et al. |
| 8,668,899 B2 | 3/2014 | Dowling et al. |
| 8,679,536 B2 | 3/2014 | Arthur |
| 8,679,537 B2 | 3/2014 | Arthur |
| 8,795,713 B2 | 8/2014 | Makower et al. |
| 8,827,980 B2 | 9/2014 | Ji |
| 8,865,150 B2 | 10/2014 | Mumper et al. |
| 8,920,364 B2 | 12/2014 | Berman et al. |
| 8,920,514 B2 | 12/2014 | Gregory et al. |
| 9,107,937 B2 | 8/2015 | Masters |
| 9,327,010 B2 * | 5/2016 | Ellis-Behnke .......... A61P 17/02 |
| 9,370,451 B2 | 6/2016 | Hardy et al. |
| 9,750,843 B2 | 9/2017 | Hardy et al. |
| 9,867,931 B2 | 1/2018 | Gittard |
| 10,080,763 B2 | 9/2018 | Bhalani et al. |
| 2001/0016577 A1 | 8/2001 | Dobrozsi et al. |
| 2002/0168334 A1 | 11/2002 | Jacob et al. |
| 2002/0169416 A1 | 11/2002 | Gonnelli |
| 2003/0008011 A1 | 1/2003 | Mershon |
| 2003/0023202 A1 | 1/2003 | Nielson et al. |
| 2003/0103932 A1 | 6/2003 | Slepian et al. |
| 2003/0108511 A1 | 6/2003 | Sawhney |
| 2003/0170250 A1 | 9/2003 | Ezrin et al. |
| 2003/0175360 A1 | 9/2003 | Luzzatti |
| 2003/0181917 A1 | 9/2003 | Gertner |
| 2003/0216695 A1 | 11/2003 | Yang |
| 2004/0009212 A1 | 1/2004 | Tsai |
| 2004/0151774 A1 | 8/2004 | Pauletti et al. |
| 2004/0156781 A1 | 8/2004 | Porter et al. |
| 2004/0225247 A1 | 11/2004 | Pugsley et al. |
| 2005/0070848 A1 | 3/2005 | Kim et al. |
| 2005/0149117 A1 * | 7/2005 | Khosravi .......... A61B 17/00491 606/215 |
| 2005/0205087 A1 | 9/2005 | Kablik et al. |
| 2005/0281775 A1 | 12/2005 | Carrington et al. |
| 2005/0281795 A1 | 12/2005 | Jolly |
| 2006/0002852 A1 | 1/2006 | Saltzman et al. |
| 2006/0052295 A1 | 3/2006 | Terman |
| 2006/0286664 A1 | 12/2006 | McAllister et al. |
| 2007/0104768 A1 | 5/2007 | Huey et al. |
| 2007/0154510 A1 | 7/2007 | Wilcher |
| 2007/0179461 A1 | 8/2007 | Sambasivam et al. |
| 2007/0179590 A1 | 8/2007 | Lu et al. |
| 2007/0207192 A1 | 9/2007 | Holl et al. |
| 2007/0240989 A1 | 10/2007 | Levitan et al. |
| 2007/0241119 A1 | 10/2007 | Durkin et al. |
| 2007/0275073 A1 | 11/2007 | Huey et al. |
| 2007/0281007 A1 | 12/2007 | Jacob et al. |
| 2007/0298087 A1 | 12/2007 | Biegajski |
| 2008/0027272 A1 | 1/2008 | Kadykowski |
| 2008/0060970 A1 * | 3/2008 | Wheeler .............. A61K 38/482 206/570 |
| 2008/0063697 A1 | 3/2008 | Bedard |
| 2008/0249506 A1 | 10/2008 | Neustaedter et al. |
| 2008/0268021 A1 | 10/2008 | Warren et al. |
| 2008/0287907 A1 | 11/2008 | Gregory et al. |
| 2008/0317831 A1 | 12/2008 | Lo |
| 2009/0010997 A1 | 1/2009 | Haley |
| 2009/0181074 A1 | 7/2009 | Makower |
| 2009/0181079 A1 | 7/2009 | Zhao et al. |
| 2009/0234374 A1 | 9/2009 | Gabel et al. |
| 2009/0234380 A1 | 9/2009 | Gabel et al. |
| 2009/0248056 A1 | 10/2009 | Gabel et al. |
| 2010/0121261 A1 | 5/2010 | Kablik et al. |
| 2010/0129427 A1 | 5/2010 | Hen et al. |
| 2010/0137796 A1 | 6/2010 | Perry et al. |
| 2010/0143481 A1 | 6/2010 | Shenoy et al. |
| 2010/0160897 A1 | 6/2010 | Ducharme et al. |
| 2010/0216754 A1 | 8/2010 | Hill |
| 2011/0097401 A1 | 4/2011 | Phillips et al. |
| 2011/0189259 A1 | 8/2011 | Vasisht et al. |
| 2011/0305768 A1 | 12/2011 | Mao et al. |
| 2012/0219612 A1 * | 8/2012 | Diegelmann ........ A61L 26/0004 424/447 |
| 2012/0237566 A1 | 9/2012 | Ray et al. |
| 2013/0039981 A1 | 2/2013 | Cherurkuri |
| 2013/0110080 A1 | 5/2013 | Duchame |
| 2013/0231753 A1 | 9/2013 | Liddy et al. |
| 2014/0105950 A1 | 4/2014 | Hardy et al. |
| 2014/0205636 A1 | 7/2014 | Khatri |
| 2014/0271491 A1 | 9/2014 | Gittard |
| 2015/0037388 A1 | 2/2015 | Longo |
| 2015/0080659 A1 | 3/2015 | Gregory et al. |
| 2015/0094649 A1 * | 4/2015 | Gittard ................. A61M 37/00 604/58 |
| 2016/0151532 A1 | 6/2016 | Rubin et al. |
| 2017/0071988 A1 | 3/2017 | Daniels et al. |
| 2017/0232141 A1 | 8/2017 | Surti et al. |
| 2018/0236123 A1 | 8/2018 | Manoryk |
| 2019/0021985 A1 | 1/2019 | Park et al. |

FOREIGN PATENT DOCUMENTS

| | | |
|---|---|---|
| CN | 102006893 A | 4/2011 |
| CN | 104507507 A | 4/2015 |
| DE | 3024749 A1 | 2/1982 |
| DE | 3108918 A1 | 9/1982 |
| DE | 3613762 A1 | 11/1987 |
| EP | 308269 A1 | 3/1989 |
| EP | 0738498 A1 | 10/1996 |
| GB | 10563 A | 12/1896 |
| GB | 1254534 A | 11/1971 |
| GB | 2 435 425 A | 8/2007 |
| JP | 4022109 B | 4/1992 |
| JP | H11501652 A | 2/1999 |
| JP | 2002338456 | 11/2002 |
| JP | 2010-508064 A | 3/2010 |
| JP | 2011507665 A | 3/2011 |
| JP | 2012/527974 | 11/2012 |
| JP | 2015-523896 A | 8/2015 |
| JP | 2016-506949 A | 3/2016 |
| JP | 2016-512069 | 4/2016 |
| JP | 2016-538895 A | 12/2016 |
| JP | 2016-539699 A | 12/2016 |
| JP | 2018-506410 A | 3/2018 |

(56) References Cited

FOREIGN PATENT DOCUMENTS

| | | |
|---|---|---|
| JP | 2020-517399 A | 6/2020 |
| SU | 978999 | 12/1982 |
| WO | WO2008/023545 | 10/1982 |
| WO | WO1985/002346 | 6/1985 |
| WO | WO1992/020312 | 11/1992 |
| WO | WO1994/028798 | 12/1994 |
| WO | WO96/21432 | 7/1996 |
| WO | WO96/25910 | 8/1996 |
| WO | WO1996/025190 | 8/1996 |
| WO | WO1996/037245 | 11/1996 |
| WO | WO1996/040327 | 12/1996 |
| WO | WO1997/020585 | 6/1997 |
| WO | WO2002/053014 | 7/2002 |
| WO | WO02/064113 | 8/2002 |
| WO | WO 2002/064113 | 8/2002 |
| WO | WO2004/002551 A2 | 1/2004 |
| WO | WO 2004/024195 A1 | 3/2004 |
| WO | WO2004/073863 | 9/2004 |
| WO | WO2005/100980 | 10/2005 |
| WO | WO 2007/074327 A1 | 7/2007 |
| WO | WO2008/008845 | 1/2008 |
| WO | WO 2008/054566 A1 | 5/2008 |
| WO | WO 2009/088726 | 7/2009 |
| WO | WO2009/091549 | 7/2009 |
| WO | WO2009/137438 A2 | 11/2009 |
| WO | WO2010/138703 | 12/2010 |
| WO | WO 2013/191836 A1 | 12/2013 |
| WO | WO 2014/119836 A1 | 8/2014 |
| WO | WO 2014/149617 | 9/2014 |
| WO | WO 2015/086640 A1 | 6/2015 |
| WO | WO 2016/022928 A1 | 2/2016 |

OTHER PUBLICATIONS

Office Action dated Apr. 24, 2018 received from the European Patent Office in European Patent Application No. 14 712 861.5.
Reporting letter received from Japanese associate dated Aug. 9, 2018 and the Office Action dated Jul. 31, 2018 received in the corresponding Japanese Patent Application No. 2016-500548.
Reporting letter received from Japanese associate dated Sep. 6, 2018 and the Office Action dated Jul. 31, 2018 received in the corresponding Japanese Patent Application No. 2016-500548.
Chinese Reporting Letter dated Aug. 16, 2018 and the Notification of Reexamination in the corresponding Chinese Application No. 201480015565.5 dated Aug. 10, 2018 (and English translation).
Patent Examination Report No. 1 dated Jan. 8, 2016 received in Australian Patent Application No. 2014237970.
Patent Examination Report No. 2 dated Oct. 14, 2016 received in Australian Patent Application No. 2014237970.
Japanese Office Action (and English translation) dated Jul. 26, 2016 received in corresponding Japanese Patent Application No. 2016-500548.
Patel et al., "Formulation and evaluation of stomach-specific amoxicillin-loaded carbopol-934P mucoadhesive microspheres for anti-Helicobacter pylori therapy," Journal of Microencapsulation, 26(4):365-376 (2009).
First Office Action received in the corresponding Chinese Patent Application No. 201480015565.5 dated May 26, 2016 (received from the Chinese associate on Jun. 7, 2016).
Bustamante-Balén, M., et al, "Role of hemostatic powders In the endoscopic management of gastrointestinal bleeding," World J of Gastrointest Pathophysiol., vol. 5(3): 284-292 (2014).
Notification of Transmittal and International Search Report and Written Opinion received in PCT Application No. PCT/US2018/029391 dated Aug. 6, 2018.
International Search Report received in PCT Application No. PCT/US2014/019893 dated May 22, 2014.
Richardson, et al., "The Bioadhesive and Swelling Characteristics of Sodium Alginate Suspensions," http://pubs.rsc.org, Oct. 21, 2009.

Potts, et al., "Oesophageal bandaging: a new opportunity for thermosetting polymers," STP Pharm S, 10(4):293-301 (2000).
Tang, et al., "Bioadhesive oesophageal bandages: protection against acid and pepsin injury," Int J. Pharm, 292(1-2):169-77 (2005).
Richardson, et al., "Oesophageal bioadhesion of sodium alginate suspensions 2. Suspension behavior on Oesophageal mucosa," Eur J Pharm Sci., 24(1):107-14 (2005).
Richardson, et al., "Oesophageal bioadhesion of sodium alginate suspensions: particle swelling and mucosal retention," Eur J Pharm Sci., 23(1):49-56 (2004).
International Preliminary Report on Patentability and Written Opinion of the International Searching Authority received in PCT Application No. PCT/US2014/019893 dated Sep. 15, 2015 (dated Sep. 24, 2015).
Japanese Office Action (and English translation) dated July 26, 2016 received in corresponding Japanese Patent Application No. 2016-500548.
Patel et al., "Formulation and evaluation of stomach-specific amoxicillin-Ioaded carbopol-934P mucoadhesive microspheres for anti-Helicobacter pylori therapy," Journal of Microencapsulation, 26(4):365-376 (2009).
Chinese Reporting Letter, Second Office Action issued in Chinese Application No. 201480015565.5 dated Jan. 12, 2017.
Office Action received in European Application No. 14 712 861.5-1455 dated Jun. 13, 2017.
Office Action dated Aug. 4, 2010 for U.S. Appl. No. 12/435,574, 7 pgs.
Response to Office Action for U.S. Appl. No. 12/435,574, filed Nov. 3, 2010, 10 pgs.
Office Action dated Feb. 17, 2011 for U.S. Appl. No. 12/435,574, 8 pgs.
Response to Office Action for U.S. Appl. No. 12/435,574, filed May 13, 2011, 11 pgs.
Office Action dated Aug. 22, 2011 for U.S. Appl. No. 12/435,574, 9 pgs.
Response to Office Action for U.S. Appl. No. 12/435,574, filed Nov. 22, 2011, 10 pgs.
Office Action dated Mar. 30, 2012 for U.S. Appl. No. 12/435,574, 9 pgs.
Response to Office Action for U.S. Appl. No. 12/435,574, filed Aug. 30, 2012, 11 pgs.
Restriction Requirement dated May 25, 2012 for U.S. Appl. No. 12/633,027, 7 pgs.
Response to Restriction Requirement filed Jul. 2, 2012 for U.S. Appl. No. 12/633,027, 7 pgs.
Office Action dated Apr. 14, 2011 for U.S. Appl. No. 12/787,796, 9 pgs.
Response to Office Action filed Jul. 14, 2011 for for U.S. Appl. No. 12/787,796, 11 pgs.
Notice of Allowance dated Oct. 18, 2011 for U.S. Appl. No. 12/787,796, 10 pgs.
International Search Report and Written Opinion for PCT/US2009/067076, dated Apr. 14, 2010, 23 pgs.
Internationai Search Report and Written Opinion for PCT/US2010/036381, dated Aug. 20, 2010, 16 pgs.
International Preliminary Report on Patentability for PCT/US2009/042781, dated Nov. 18, 2010, 11 pgs.
International Search Report completed Sep. 22, 2009 for PCT/US2009/042781, 7 pgs.
Alto Shooter Catalog, Kaigen, English and Japanese, Jun. 1994, 8 pgs.
Decker, "An Efficient Method For The Application Of Avitene Hemostatic Agent", Surgery, Gynecology & Obstetrics, 1991, vol. 172, No. 6, 2 pgs.
Endo-Avitene brochure, Med Chem Products, Inc., date unknown, 4 pgs.
Fagelman, et al. "A Simple Method For Application Of Microfibrilar Colagen", Surgery, Gynecology & Obstetrics, Jun. 1980, vol. 150, No. 6, 3 pgs.
Hoshino, et al. "Trans-endoscopic Drug Propulsion Therapy", Diagnostic Endoscopy, 1993, vol. 5, 6 pgs.
Surgical Armamentarium, Copyright 1973 V. Mueller, 3 pgs.

(56) References Cited

OTHER PUBLICATIONS

Hoshino, "Transendoscopic Projectile Drug Delivery", Gastroenterologia Japonica, vol. 25, No. 5, Jun. 15, 1990, 1 page.
Park et al., "A randomized comparison of a new flexible bipolar hemostasis forceps designed principally for NOTES versus a conventional surgical laparoscopic bipolar forceps for intra- abdominal vessel sealing in a porcine model", Gastrointestinal Endoscopy 2010, vol. 71, No. 4, pp. 835-841.
Fritscher-Ravens et al., "Beyond NOTES: randomized controlled study of different methods of flexible endoscopic hemostasis of artifically induced hemorrhage, via NOTES access to the peritoneal cavity", Endoscopy 2009, vol. 41, pp. 29-35.
Final Office Action for U.S. Appl. No. 12/435,574 dated Feb. 17, 2011, 8 pgs.
Examiner Interview Summary for U.S. Appl. No. 12/435,574 dated Jun. 10, 2011, 3 pgs.
Notice of Appeal for U.S. Appl. No. 12/435,574, filed Aug. 17, 2011, 1 pg.
Notice of Allowance dated Oct. 5, 2012 for US. Appl. No. 12/633,027, 9 pgs.
International Preliminary Report on Patentability for PCT/US2009/067076 dated Jun. 29, 2011, 12 pgs.
International Preliminary Report on Patentability for PCT/US2010/036381 dated Nov. 29, 2011, 7 pgs.
Examination Report for Australian Patent Application No. 2009244462 dated Sep. 27, 2012; 4 pgs.
Response to Examination Report for Australian Patent Application No. 2009244462 filed Feb. 19, 2013; 8 pgs.
Examination Report for Canadian Patent Application No. 2,723,183 dated Aug. 17, 2012, 2 pgs.
Response to Examination Report for Canadian Patent Application No. 2,723,183 filed Feb. 11, 2013, 5 pgs.
Examination Report for European Patent Application No. 09743424.5 dated Nov. 14, 2011, 5 pgs.
Response to Examination Report for European Patent Application No. 09743424.5 filed Mar. 14, 2012, 10 pgs.
Examination Report for European Patent Application No. 09743424.5 dated Sep. 5, 2012, 6 pgs.
Response to Examination Report for European Patent Application No. 09743424.5 filed Feb. 22, 2013, 4 pgs.
Office Action for U.S. Appl. No. 13/351,524 dated Oct. 18, 2012, 14 pgs.
Examiner Interview Summary for U.S. Appl. No. 13/351,524 dated Feb. 8, 2013, 4 pgs.
Response to Office Action for U.S. Appl. No. 13/351,524, filed Feb. 12, 2013, 9 pgs.
Office Action for JP2016-520011 dated May 2, 2017, 7 pgs. Including English translation.
First Australian Examination Report for related AU Application No. 2014329827, dated Aug. 29, 2016, 4 pgs.
Reply to First Australian Examination Report for related AU Application No. 2014329827, dated Nov. 10, 2016, 16 pgs.
Notice of Acceptance for Patent Application for related AU Application No. 2014329827, dated Dec. 12, 2016, 3 pgs.
Canadian Examination Report for related CA Application No. 2,925,900, dated Feb. 23, 2017, 4 pgs.
European Communication Pursuant to Rule 161 (1) and 162 for related EP Application No. 14789657.5, dated May 11, 2016, 2 pgs.
Reply to European Communication Report, dated Nov. 10, 2016, 8 pgs.
PCT International Search Report and Written Opinion for related Application No. PCT/US2014/058016, dated Apr. 21, 2015, 15 pgs.
Endo-Avitene™ Brochure "Microfibrillar Collagen Hemostate in an Endoscopic Delivery System," from MedChem Products. 4 pgs, 1992.
Chinese Reporting Letter, Third Office Action issued in Chinese Application No. 201480015565.5 dated Apr. 6, 2017.
Chinese Reporting Letter, Rejection Decision (and English translation) issued in Chinese Application No. 201480015565.5 dated Sep. 8, 2017.
Giday, Samuel A., "Preliminary Data on the Nanopowder Hemostatic Agent TC-325 to Control Gastrointestinal Bleeding," Gastroenterology & Hepatology, 7(9):620-622 (Sep. 2011).
Office Action dated Apr. 2, 2015 for U.S. Appl. No. 14/209,718, 13 pgs.
Response to Office Action filed Jul. 2, 2015 for U.S. Appl. No. 14/209,718, 16 pgs.
Office Action dated Aug. 10, 2015 for U.S. Appl. No. 14/209,718, 12 pgs.
European Communication Pursuant to Rule 161 (1) and 162 for related EP Application No. 14712861.5, dated Oct. 22, 2015, 2 pgs.
Response to Office Action filed Nov. 5, 2015 for U.S. Appl. No. 14/209,718, 16 pgs.
Advisory Action dated Dec. 16, 2015 for U.S. Appl. No. 14/209,718, 4 pgs.
Response to Advisory Action filed Jan. 25, 2016 for U.S. Appl. No. 14/209,718, 19 pgs.
Response to Rule 161 Communication for European Patent Application No. 14712861.5 filed Apr. 28, 2016; 11 pgs.
Office Action dated Sep. 14, 2016 for U.S. Appl. No. 14/209,718, 19 pgs.
Response to Office Action filed Dec. 14, 2016 for U.S. Appl. No. 14/209,718, 34 pgs.
Notice of Acceptance for Patent Application dated Dec. 20, 2016 for Australian Patent Application No. 2014237970, 3 pgs.
Office Action dated Apr. 18, 2017 for U.S. Appl. No. 14/209,718, 23 pgs.
Report of the pre-appeal re-examination dated Jun. 9, 2017 for Japanese Patent Application No. 2016-500548, 7 pgs, and the accompanying, reporting letter from the Japanese associate dated Jun. 20, 2017 and a follow up letter dated Jul. 21, 2019.
Response to Office Action filed Jun. 15, 2017 for U.S. Appl. No. 14/209,718, 18 pgs.
Chinese Reporting Letter, Fourth Office Action issued in Chinese Application No. 201480015565.5 dated Jun. 28, 2017.
Advisory Action dated Jul, 20, 2017 for U.S. Appl. No. 14/209,718, 3 pgs.
Response to Office Action filed Aug. 15, 2017 for U.S. Appl. No. 14/209,718, 21 pgs.
Rejection Decision dated Sep. 8, 2017 for Chinese Patent Application No. 20148001565.5, 18 pgs.
Response to European Office Action for Patent Application No. 14712861.5 filed Dec. 20, 2017; 12 pgs.
Office Action dated Apr. 2, 2018 for U.S. Appl. No. 14/209,718, 21 pgs.
Response to Office Action filed Jun. 28, 2018 for U.S. Appl. No. 14/209,718, 24 pgs.
Office Action dated Aug. 7, 2018 for Japanese Patent Application No. 2016-500548, 12 pgs.
Response to European Office Action for Patent Application No. 14712861.5 filed Aug. 29, 2018; 29 pgs.
Office Action dated Dec. 14, 2018 received from the European Patent Office in European Patent Application No. 14 712 861.5, 6 pgs.
Office Action issued in Japanese Application No. 2016-500548 dated Jan. 15, 2019, 12 pages.
Office Action dated Feb. 8, 2019 for U.S. Appl. No. 14/209,718, 28 pgs.
Examiner Interview Summary dated Feb. 28, 2019 for U.S. Appl. No. 14/209,718, 3 pgs.
International Preliminary Report on Patentability and Written Opinion of the International Searching Authority dated Oct. 29, 2019 for corresponding Application PCT/US2018/029391.
First Office Action received in the corresponding Japanese Patent Application No. 2019-558626 dated Nov. 4, 2020, and a letter from the Japanese associate dated Nov. 6, 2020 reporting the First Office Action.
Reporting Letter dated Jun. 10, 2021 enclosing the Decision for Rejection received in Japanese Patent Application No. 2019-558626 dated Jun. 8, 2021.
Reporting Letter dated Jun. 2, 2021 enclosing the Preliminary Rejection received in Korean Patent Application No. 10-2019-

(56) References Cited

OTHER PUBLICATIONS 7034882 dated May 24, 2021 (in Korean and including English translation of the Preliminary Rejection).
Office Action in Corresponding European Application No. 18724076.7, dated Oct. 25, 2021 (9 pages).
Office Action and English Translation in Corresponding Chinese Application No. 20188003547848, dated Jun. 9, 2021 (9 pages).
Response to First Office Action in Corresponding Chinese Application No. 2018800357848, dated Sep. 17, 2021 (12 pages).
Second Office Action and English Translation in Corresponding Chinese Application No. 2018800357848, dated Dec. 1, 2021 (8 pages).
Response to Second Office Action in Corresponding Chinese Application No. 2018800357848, dated Feb. 10, 2022 (4 pages).
Third Office Action and English Translation in Corresponding Chinese Application No. 2018800357848, dated Mar. 29, 2022 (9 pages).
Response to Examination Report in Corresponding European Application No. 18724076.7, dated Feb. 25, 2022 (12 pages).
First Office Action and English translation in Corresponding Japanese Application No. 2021-165391, dated Oct. 4, 2022 (11 pages).
Office Action in Japanese Application No. 2021-165391, dated Mar. 7, 2023 (8 pages).
Office Action in Japanese Application No. 2022-521497, dated Mar. 22, 2023 (5 pages).
Office Action in Chinese Application No. 202080070938.4, dated Apr. 29, 2023 (14 pages).

\* cited by examiner

BIMODAL TREATMENT METHODS AND COMPOSITIONS FOR GASTROINTESTINAL LESIONS WITH ACTIVE BLEEDING

RELATED APPLICATIONS

The present patent document is a continuation-in-part application of U.S. patent application Ser. No. 14/209,718, filed Mar. 13, 2014, which claim the benefit of the filing date under 35 U.S.C. § 119(e) of Provisional U.S. Patent Application Ser. No. 61/793,586, filed Mar. 15, 2013, and the present patent document is a continuation-in-part application of U.S. patent application Ser. No. 14/044,040, filed Oct. 2, 2013, which are hereby incorporated by reference.

BACKGROUND

1. Technical Field

Medical products and methods for delivering therapeutic agents and treating lesions in the gastrointestinal tract, such as lesions arising from the disorders of the gastrointestinal tract and or medical procedures that require removal of the mucosal or submucosal layers of gastrointestinal tract wall are described.

2. Background Information

There are several instances in which it may become desirable to introduce therapeutic agents into the human or animal body. For example, therapeutic drugs or bioactive materials may be introduced to achieve a biological effect. The biological effect may include an array of targeted results, such as inducing hemostasis, sealing perforations, reducing restenosis likelihood, or treating cancerous tumors or other diseases.

There are several disorders of the gastrointestinal tract, e.g., gastrointestinal inflammation, gastrointestinal cancer, gastrointestinal infection, gastrointestinal motility dysfunction, or lesions, wounds or contusions of tissue of a portion of the gastrointestinal tract that can cause gastrointestinal lesions. In addition, there are a wide variety of medical procedures that require removal of the mucosal or submucosal layers of gastrointestinal tract wall and can also cause injury or lesions in the gastrointestinal tract. These procedures include endoscopic mucosal resection (EMR), endoscopic submucosal dissection, polypectomy, per-oral endoscopic myotomy, biopsy, and ablation (thermal, chemical, radiofrequency, and cryogenic). As with the disorders of the gastrointestinal tract, similar adverse events can occur after removal of the mucosal or submucosal layers, including bleeding and structuring.

Many of the therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites. For example, localized delivery of therapeutic agents to a tumor may reduce the exposure of the therapeutic agents to normal, healthy tissues, which may reduce potentially harmful side effects.

Localized delivery of therapeutic agents has been performed using catheters and similar introducer devices. By way of example, a catheter may be advanced towards a target site within the patient, then the therapeutic agent may be injected through a lumen of the catheter to the target site. Typically, a syringe (with or without a needle) or similar device may be used to inject the therapeutic agent into the lumen of the catheter. However, such a delivery technique may result in a relatively weak stream of the injected therapeutic agent.

Moreover, it may be difficult or impossible to deliver therapeutic agents in a targeted manner in certain forms, such as a powder form, to a desired site. For example, if a therapeutic powder is held within a syringe or other container, it may not be easily delivered through a catheter to a target site in a localized manner that may also reduce potentially harmful side effects.

Use of mucoadhesives and bioadhesives including various chemical derivatives of chitosan, Carbopol™ and polycarbophil has been known to open epithelial tight junctions, prevent intestinal ulceration, retain drugs in open wounds, increase ocular-surface residence, and have vaccine adjuvant activity, however, the use of mucoadhesives for the treatment of gastrointestinal lesion has not been previously proposed or documented.

Currently, the standard approach for treating gastrointestinal lesions is to use clips to fold the tissue upon itself, thus isolating the lesion from the gastrointestinal environment. However, this method has a poor success rate (10-20% failure), is expensive, and technically challenging.

As such, new or improved devices and methods for long-term localized treatment to address the issues arising from the disorders of the gastrointestinal tract and or medical procedures that require removal of the mucosal or submucosal layers of gastrointestinal tract wall are highly desirable.

SUMMARY

One embodiment relates to a multi-layer coating for achieving hemostasis of an actively bleeding lesion and maintaining hemostasis of said lesion, comprising: (i) a hemostatic layer, comprising a hemostatic agent in the form of a liquid, gel, or powder in direct contact with the actively bleeding lesion; and (ii) a protective covering, comprising an adhesive agent in the form a liquid, gel, or powder in direct contact with both, the hemostatic layer and the surrounding tissue, wherein the protective covering is capable of remaining at and about a site of the lesion for a minimum of 30 minutes. The hemostatic layer and the protective covering are delivered at and about the site of the lesion by flowing through a catheter. The lesion may be a mucosal lesion. The adhesive agent may be a mucoadhesive agent selected from the group consisting of carbomers, polycyclic aromatic hydrocarbons, carboxylic acids, polyvinylpyroolidones, polyvinylalchohols, polycarbophils, chitosan material, sodium alginates, cellulose derivatives, ethers, lectins, thiamines, pathogenic bacteria, thiols, amino acid sequences, ion-exchange resins, any biomolecules including an amino acid sequence, mucin, guar gum, karya gum, xantham gum, locust bean gum, acacia gum, gellan gum, tragacanth, soluble starch, gelatin, pectin, and any biomolecules having an affinity for a mucosa. The multi-layer coating is a minimum of 0.1 mm in thickness. The hemostatic agent may be selected from the group consisting of thrombin, epinephrine, sclerosant, and absorbent clays (e.g., laponite, smectites, zeolites, kaolin). The hemostatic agent may be a hemostatic clay. The protective covering may further comprise a pH modifier. The protective covering may be capable of remaining at and about the site of the lesion for a minimum of 24 hours; for a minimum of 48 hours; or for a minimum of 72 hours. The protective covering may be in the form of a powder, wherein the powder consists of particles comprised of adhesive particles and barrier forming particles that are bound together.

Another embodiment relates to a method for protecting and treating a lesion with active bleeding in the gastrointestinal tract, comprising: (i) directly applying a hemostatic composition comprising a hemostatic agent at and about a site of the lesion in the gastrointestinal tract in the amount and for a time sufficient to stop the active bleeding; and (ii) once the active bleeding has stopped or slowed, directly applying a protective covering comprising an adhesive agent on top of and about at least a portion of the previously applied hemostatic composition, wherein the protective covering upon application on top of and about at least a portion of the hemostatic composition is in direct contact with both, the hemostatic composition and tissue surrounding the lesion, provides a sustained protective barrier, and is capable of remaining at and about the site of the lesion for a minimum of 30 minutes. The applying step (i) may comprise spraying, ejecting or spreading the hemostatic agent at and about the site of the lesion with the active bleeding. The applying step (ii) may comprise spraying, ejecting or spreading the protective covering on top of and about at least a portion of the previously applied hemostatic composition at and about the lesion site in the gastrointestinal tract. The adhesive agent may be in a powder, a liquid or a gel form. The adhesive agent may be a mucoadhesive agent. The adhesive agent may be a mucoadhesive agent selected from the group consisting of carbomers, polycyclic aromatic hydrocarbons, carboxylic acids, polyvinylpyroolidones, polyvinylalchohols, polycarbophils, chitosan material, sodium alginates, cellulose derivatives, ethers, lectins, thiamines, pathogenic bacteria, thiols, amino acid sequences, ion-exchange resins, any biomolecules including an amino acid sequence, mucin, guar gum, karya gum, xantham gum, locust bean gum, acacia gum, gellan gum, tragacanth, soluble starch, gelatin, pectin, and any biomolecules having an affinity for a mucosa. The protective covering may comprise a solid material in a form of a bandage, a patch, or a dressing. The protective covering may be adapted for delivery in a liquid form that solidifies upon the delivery on top of and about at least a portion of the hemostatic composition at and about the lesion site. The method may further comprise applying a crosslinking initiator selected from the group consisting of chemical, thermal, light, curing agent, and a catalyst. The method may further include: instructing a medical practitioner to apply the hemostatic agent to and about the site of the lesion with the active bleeding in the gastrointestinal tract first; instructing the medical practitioner to determine whether the active bleeding has stopped; and instructing the medical practitioner to apply the protective covering on top of and about at least a portion of the hemostatic composition at and about the lesion site in the gastrointestinal tract.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Long-lasting adhesive medical products and methods for protecting or treating lesions in the gastrointestinal tract resulting from disorders of the gastrointestinal tract and/or medical procedures that require removal of the mucosal or submucosal layers of gastrointestinal tract, such as, for example, endoscopic submucosal dissection (ESD), endoscopic mucosal resection, polypectomy, ulcer, cancer, varices, Barrett's esophagus ablation, or a combination thereof, are described herein.

Also, long-lasting medical products and methods for protecting or treating lesions in the gastrointestinal tract with active bleeding resulting from disorders of the gastrointestinal tract and/or medical procedures that require removal of the mucosal or submucosal layers of gastrointestinal tract, such as, for example, ESD, endoscopic mucosal resection, polypectomy, ulcer, cancer, varices, Barrett's esophagus ablation, or a combination thereof, are described herein.

The long-lasting adhesive medical products (i.e., a multi-layer coating for achieving hemostasis of an actively bleeding lesion and maintaining hemostasis of the lesion) described herein include two components, (i) a composition comprising a hemostatic agent (also referred to as a "hemostatic composition" or "hemostatic layer" throughout this application), and (ii) a protective covering comprising an adhesive agent (referred to as a "protective covering" throughout this application). The two components may be, for example, in a form of a powder, a gel, or a liquid, or may be a solid material, such as a bandage, a dressing, a patch or the like. For example, the hemostatic layer includes a hemostatic agent in the form of a liquid, gel, or powder in direct contact with the actively bleeding lesion. For example, the protective covering includes an adhesive agent in the form a liquid, gel, or powder in direct contact with both, the hemostatic layer and the surrounding tissue. The multi-layer coating is a minimum of 0.1 mm in thickness.

The hemostatic composition and the protective coating are delivered separately to and about a site of a lesion with active bleeding in the gastrointestinal tract. The hemostatic composition is delivered first and applied to the lesion with the active bleeding to slow or stop bleeding, and/or prevent delayed bleeding; the protective covering is delivered after the hemostatic composition is delivered and once the active bleeding has stopped or slowed, and applied on top of, over and/or about the hemostatic composition (i.e., so that the protective covering is in direct contact with both, the hemostatic layer and the surrounding tissue) to protect or treat the lesion from further injury or infection, prevent delayed perforation, prevent rebleeding, seal anastomotic leaks or fistulas, and/or promote healing at the exposed site.

The hemostatic composition functions to reduce or stop active bleeding from lesions by creating a mechanical barrier over the bleeding site; the protective covering that includes an adhesive agent, helps protect these lesions from complications, such as rebleeding, ulcer formation, scar formation, and stricturing. A method of combining both of these treatments as "bimodal therapy" for gastrointestinal lesions with active bleeding is described herein.

As such, certain embodiments relate to long-lasting adhesive medical products and methods for protecting or treating lesions with active bleeding in the gastrointestinal tract. The term "hemostatic composition" refers to a composition that includes a hemostatic agent that may be any antihemorrhagic agent that promotes hemostasis (i.e., stops, slows or reduces bleeding). Locally-acting hemostatic agents work by causing vasoconstriction or promoting platelet aggregation. Exemplary hemostatic agents include organic agents, such as microfibrillar collagen, thrombin, and chitosan; natural, plant-based polysaccharides, such as various starches, such as modified and unmodified starches (e.g., potato starch); inorganic agents, such as absorbent clays (e.g., laponite, smectites, zeolites, kaolin); styptics; amylopectin, including a modified (cross-linked) pregelatinized amylopectin. Other hemostatic agents that may be used may include epinephrine, sclerosant, sephadex and debrisan. Natural plant based polysaccharides tend to be biocompatible, bisorbable and free of animal components. While plant-based polysaccharides are preferred as hemostatic agents, gelatin and other animal-derived polysaccharides may also be used.

The terms "protective coating" or "coating" or "protective covering" or "covering" encompass a powder and/or a liquid coating (e.g., solid, powder, liquid or gel suitable for applying, e.g., by spraying or coating or other known methods at and about the site of the lesion, where the liquid or gel coatings solidify at the site), as well as, a solid material, such as a bandage, a dressing, a patch and the like. Specifically, the terms encompass powder, liquid and gel coatings and solid materials (e.g., bandages, dressings, patches) for use in treating or protecting lesions in the gastrointestinal tract. Protective covering includes an adhesive agent, such as a mucoadhesive agent. Exemplary mucoadhesive agents include carbomers, polycyclic aromatic hydrocarbons, carboxylic acids, polyvinylpyroolidones, polyvinylalchohols, polycarbophils, chitosan material, sodium alginates, cellulose derivatives, ethers, lectins, thiamines, pathogenic bacteria, thiols, amino acid sequences, ion-exchange resins, any biomolecules including an amino acid sequence, mucin, guar gum, karya gum, xantham gum, locust bean gum, acacia gum, gellan gum, tragacanth, soluble starch, gelatin, pectin, and any biomolecules having an affinity for a mucosa.

The term "lesion" refers to any tissue defect or bodily injury with disruption of the normal integrity of tissue structures and/or a pathological change in a bodily organ or tissue, and specifically, any bodily organ or tissue in the gastrointestinal tract. The term is also intended to encompass the terms "wound," "injury," "sore," "necrosis" and "ulcer," especially, a wound, injury, sore, necrosis and an ulcer with an active bleeding. The term "sore" typically refers to any lesion of the mucous membranes. The term "ulcer" refers to a local defect, or excavation, of the surface of an organ or tissue in the gastrointestinal tract, which is produced by the sloughing of necrotic tissue. The term "necrosis" relates to dead tissue resulting from infection, injury, inflammation or infarctions. The lesion may be any lesion due to disorders of the gastrointestinal tract and or medical procedures that require removal of the mucosal or submucosal layers of gastrointestinal tract wall. For example, a lesion may be due to endoscopic submucosal dissection, endoscopic mucosal resection, polypectomy, ulcer, cancer, varices, Barrett's esophagus ablation, or a combination thereof, that resulted in active bleeding.

The term "active bleeding" refers to all forms of bleeding in the gastrointestinal tract. It is also knows as gastrointestinal hemorrhage. The bleeding in the gastrointestinal tract may be anywhere in the tract, from the mouth to the rectum. When there is significant blood loss over a short time, symptoms may include vomiting red blood, vomiting black blood, bloody stool, or black stool.

The phrases "to and about" or "at and about" in connection with the delivery of the hemostatic composition and the protective covering mean that the hemostatic composition and/or the protective covering is placed on the lesion itself, including within the lesion, as well as just immediately around the lesion to ensure as most complete coverage of the lesion as possible.

The phrases "on top of and about" or "over and about" in connection with the delivery of the protective covering mean that the protective covering is placed on top of the previously applied hemostatic composition at the lesion as well as just immediately around the hemostatic composition and the lesion to ensure as most complete coverage of the lesion as possible.

Specifically, in the described methods for protecting or treating a lesion with active bleeding in the gastrointestinal tract, the hemostatic composition is delivered first and applied locally/directly at and about a site of the lesion in the gastrointestinal tract to stop the active bleeding at the lesion; and once the active bleeding has stopped or slowed, a protective covering comprising an adhesive agent is locally and directly applied on top of, over and about at least a portion of the hemostatic composition at and about the lesion site in the gastrointestinal tract. The protective covering upon application over and about at least a portion of hemostatic composition at and about the site of the lesion adheres to the gastrointestinal tissue, provides a sustained protective barrier, and is capable of remaining at and about the site of the lesion for a minimum of 30 minutes.

Specifically, upon a direct and localized delivery of the long-lasting protective covering described herein over and about the hemostatic composition at and about a site of a lesion with active bleeding, it will form a protective covering at and about the site of the lesion by at least partially or completely covering the hemostatic composition and the lesion. The protective covering remains at and about the lesion site for a time sufficient to allow the site to be treated or healed (minimum of 30 minutes; preferably 24 hours; more preferably at least 48 or 72 hours; most preferably the protective covering is capable of remaining at and about the lesion site for 24-72 hours or longer; hence the term "long-lasting" refers to the time period that a protective covering of the present invention remains at and about the lesion and means anywhere from 30 minutes to 72 hours or longer). The term "protect" refers to protecting the site of the lesion from further injury or infection. The term "treat" refers to slowing or stopping bleeding at the site of the lesion, preventing delayed bleeding, preventing delayed perforation of the lesion, and/or promoting healing at the exposed site of the lesion, and/or promoting new tissue formation. The term "heal" in reference to a lesion refers to a process of repairing the gastrointestinal tissue by natural processes, as by, for example, scar formation so that following "healing" the lesion is at least reduced in size as compared to the initial size of the lesion or absent.

One embodiment relates to a multi-layer coating for achieving hemostasis of an actively bleeding lesion and maintaining hemostasis of said lesion, comprising: (i) a hemostatic layer, comprising a hemostatic agent in the form of a liquid, gel, or powder in direct contact with the actively bleeding lesion; and (ii) a protective covering, comprising an adhesive agent in the form a liquid, gel, or powder in direct contact with both, the hemostatic layer and the surrounding tissue, wherein the protective covering is capable of remaining at and about a site of the lesion for a minimum of 30 minutes. The hemostatic layer and the protective covering are delivered at and about the site of the lesion by flowing through a catheter. The lesion may be a mucosal lesion. The covering is a minimum of 0.1 mm in thickness. The protective covering may further comprise a pH modifier. The protective covering may be capable of remaining at and about the site of the lesion for a minimum of 24 hours; for a minimum of 48 hours; or for a minimum of 72 hours. The protective covering may be in the form of a powder, wherein the powder consists of particles comprised of adhesive particles and barrier forming particles that are bound together.

The hemostatic layer includes a hemostatic agent that may be any antihemorrhagic agent that promotes hemostasis (i.e., stops, slows or reduces bleeding). Exemplary hemostatic agents include organic agents, such as microfibrillar collagen, thrombin, and chitosan; natural, plant-based polysaccharides, such as various starches, such as modified and unmodified starches (e.g., potato starch); inorganic agents, such as absorbent clays (e.g., laponite, smectites, zeolites, kaolin); styptics; amylopectin, including a modified (cross-linked) pregelatinized amylopectin. Other hemostatic agents that may be used may include epinephrine, sclerosant, sephadex and debrisan. Natural plant based polysaccharides tend to be biocompatible, bisorbable and free of animal components. While plant-based polysaccharides are preferred as hemostatic agents, gelatin and other animal-derived polysaccharides may also be used. In certain embodiments, the hemostatic agent is a hemostatic clay.

In certain embodiments, the protective covering includes an adhesive agent.

An adhesive agent may include any currently known or future developed tissue adhesive agent(s). The adhesive may be a mucoadhesive or any other type of tissue adhesive. A mucoadhesive agent is preferred. As used herein, the terms "a mucoadhesive" or "a mucoadhesive agent" refer to an agent that adheres to a mucous membrane, which may line the wall of a body vessel or body cavity, e.g., a gastrointestinal surface (e.g., either or both of a gastrointestinal epithelia or mucosa (including submucosa) and, specifically, at and about a site of a lesion. The mucous membrane may include a moist mucous layer to which the mucoadhesive agent may adhere. Generally, mucoadhesive agents are hydrophilic macromolecules containing numerous functional groups capable of forming hydrogen bonds.

One example of a mucoadhesive agent suitable for use herein includes a macromolecule (e.g., a polymer) including repeating monomer units. Other examples of mucoadhesive agents for use in the long-lasting adhesive medical product of the present invention include, for example, a hydrophilic polymer, a hydrogel, a co-polymer, or a thiolated polymer. The hydrogen bond forming functional groups may include carboxyl groups, hydroxyl groups, carbonyl groups, sulphate groups, amide groups, or any other functional groups capable of forming hydrogen bonds. Examples of mucoadhesive agents or components thereof may include, for example, carbomers (e.g., polyacrylic acids), polycyclic aromatic hydrocarbons (e.g., retene), carboxylic acids, polyvinylpyroolidones, polyvinylalchohols, polycarbophils, chitosan materials (i.e., poliglusam, deacetylchitin, or poly-(D) glucosamine), sodium alginates, cellulose derivatives (e.g., methylcellulose, methylethylcellulose, sodium carboxymethylcellulose, hydroxypropylcellulose, hydroxypropylmethylcellulose, or hydroxyethylcellulose), ethers (e.g., polyethylene glycol), lectins (e.g., Erythrina c. lectin, Concanavalin a. lectin, Ulex europaeus lectin, and C-Type lectin), thiamines (e.g. thiamine end capped polymer chains); pathogenic bacteria (e.g., bacterial fimbrins), thiols (e.g. chitosan-cysteine, chitosan-thiolbutylamidine, chitosan-thioglycolic acid, polyacrylic acid-cysteine, polyacrylic acid-cysteamine, carboxymethylellulose-cystein, or alginate-cysteine), amino acid sequences, ion-exchange resins (e.g., cholestyramine), or any biomolecules including an amino acid sequence (e.g. peptides). Additional examples of mucoadhesive agents or components thereof may include mucin, guar gum, karya gum, xantham gum, locust bean gum, acacia gum, gellan gum, tragacanth, soluble starch, gelatin, or pectin. In some examples, mucoadhesive agents may include any biomolecules having an affinity for mucosal tissue such as, for example, proteins (e.g., fimbrial proteins or affinity ligands).

A mucoadhesive agent adheres to the hemostatic composition and/or a mucous membrane by physical and/or chemical forces including, for example, ionic bonding, covalent bonding, hydrogen bonding, Van-der-Waals bonding, or hydrophobic bonding (i.e., hydrophobic interaction).

Other types of tissue adhesives include cyanoacrylate glues and sealants, glutaraldehyde, DOPA, or any other known polymer or biological adhesives.

In certain embodiments, the protective covering may comprise a mucoadhesive agent that may be in the form of a powder, a solid solution, an emulsion, a liquid or semi-liquid solution, a liquid suspension, a gel, a foam, or a combination thereof. Other known types of formulations may also be suitable for use and will be known to a skilled artisan. The protective covering may also transition between multiple forms or phases previously described.

The amount of the hemostatic composition and the protective covering to be administered to and about the lesion with active bleeding will depend on the type and size of the lesion, the form of the hemostatic and mucoadhesive agents used and the delivery system used to deliver the hemostatic and mucoadhesive agents. For example, if the hemostatic composition and/or protective covering are in the powder form, anywhere from a few tenths of a gram to several grams (e.g., anywhere from about 0.01 grams to about 60 grams) may be delivered of each component and placed on and about the lesion site to provide a sufficient coverage at and about the lesion site with active bleeding, e.g., 10 microns to 2 mm thick. When a hemostatic composition is delivered, anywhere from a few tenths of a gram to several grams (e.g., anywhere from about 0.01 grams to about 25 grams) may be delivered and placed on and about the lesion site to provide a sufficient coverage at and about the lesion site with an active bleeding and to stop the bleeding. More typically, about 2 grams of the hemostatic composition and/or protective covering would be sufficient to stop the bleeding and coat the lesion site, respectively (to achieve a thickness of anywhere from 10 microns to 2 mm thick). If the hemostatic composition and/or the protective covering are in a gel or a liquid form, enough of both components are provided at and about the lesion to stop the active bleeding, and allow sufficient coverage of the lesion, respectively, e.g., at least 10 microns to 2 mm thick.

The amount of the hemostatic and/or mucoadhesive agents in the liquid or gel forms may vary from 0.1 to 99.5%.

In certain embodiments, any hemostatic composition described herein comprises greater than about 0.1% w/w, greater than about 0.2% w/w, greater than about 0.5% w/w, greater than about 1% w/w, greater than about 2% w/w, greater than about 3% w/w, greater than about 4% w/w, greater than about 5% w/w, greater than about 6% w/w, greater than about 7% w/w, greater than about 8% w/w, greater than about 9% w/w, greater than about 10% w/w, greater than about 11% w/w, greater than about 12% w/w, greater than about 13% w/w, greater than about 14% w/w, greater than about 15% w/w, greater than about 16% w/w, greater than about 17% w/w, greater than about 18% w/w, greater than about 19% w/w, greater than about 20% w/w, greater than about 21% w/w, greater than about 22% w/w, greater than about 23% w/w, greater than about 24% w/w, greater than about 25% w/w, greater than about 26% w/w, greater than about 27% w/w, greater than about 28% w/w, greater than about 29% w/w, greater than about 30% w/w, greater than about 35% w/w, greater than about 40% w/w, greater than about 45% w/w, greater than about 50% w/w, greater than about 55% w/w, greater than about 60% w/w, greater than about 65% w/w, greater than about 70% w/w, greater than about 80% w/w, greater than about 85% w/w, greater than about 90% w/w, greater than about 95% w/w, or greater than about 99.5% w/w of hemostatic agent that can stop the active bleeding at the lesion in the gastrointestinal tract (e.g., the surface of the stomach).

In certain embodiments, any protective covering described herein comprises greater than about 0.1% w/w, greater than about 0.2% w/w, greater than about 0.5% w/w, greater than about 1% w/w, greater than about 2% w/w, greater than about 3% w/w, greater than about 4% w/w, greater than about 5% w/w, greater than about 6% w/w, greater than about 7% w/w, greater than about 8% w/w, greater than about 9% w/w, greater than about 10% w/w, greater than about 11% w/w, greater than about 12% w/w, greater than about 13% w/w, greater than about 14% w/w, greater than about 15% w/w, greater than about 16% w/w, greater than about 17% w/w, greater than about 18% w/w, greater than about 19% w/w, greater than about 20% w/w, greater than about 21% w/w, greater than about 22% w/w, greater than about 23% w/w, greater than about 24% w/w, greater than about 25% w/w, greater than about 26% w/w, greater than about 27% w/w, greater than about 28% w/w, greater than about 29% w/w, greater than about 30% w/w, greater than about 35% w/w, greater than about 40% w/w, greater than about 45% w/w, greater than about 50% w/w, greater than about 55% w/w, greater than about 60% w/w, greater than about 65% w/w, greater than about 70% w/w, greater than about 80% w/w, greater than about 85% w/w, greater than about 90% w/w, greater than about 95% w/w, or greater than about 99.5% w/w of mucoadhesive that can extend the time the covering is in contact with a surface of the gastrointestinal tract (e.g., the surface of the stomach) and protects or treats the lesion from further injury or infection, prevents delayed perforation, prevents delayed or recurrent bleeding, seals anastomotic leaks or fistulas, and/or promotes healing at the exposed site.

As provided herein, the hemostatic composition and/or protective covering in a form of a powder may include finely divided or subdivided preparations, coarsely comminuted products, or products of intermediate particle size. The components in a form of a powder can comprise particles which are very coarse, of the dimensions of about 10,000 microns or 10 mm, or particles which are extremely fine, approaching dimensions of about 1 micron or less, or particles of any size in between coarse and fine. The size of the particles will depend on the type of hemostatic and mucoadhesive agents used in the composition and protective covering, respectively, and may be highly variable especially for the granular mucoadhesive.

In addition, powders can contain certain proportions of liquids dispersed thoroughly and uniformly over the solid components of the mixture, or can be composed entirely of solid materials.

In certain embodiments, the hemostatic composition may include one or more hemostatic agents. For example, a hemostatic composition in a form of a powder can be a physical admixture of two or more powdered pure hemostatic agents present in definite or differing proportions. For example, a hemostatic composition in a form of a liquid can be a physical admixture of two or more powdered pure hemostatic agents present in definite or differing proportions mixed with a solvent.

In certain embodiments, the protective covering may include one or more mucoadhesive agents. For example, a protective covering in a form of a powder can be a physical admixture of two or more powdered pure mucoadhesive agents present in definite or differing proportions. For example, a protective covering in a form of a liquid can be a physical admixture of two or more powdered pure mucoadhesive agents present in definite or differing proportions mixed with a solvent.

In some embodiments, therapeutic agents and or the excipients may be mixed in with the hemostatic and/or mucoadhesive powders into formulations suitable for use according to the methods of this invention or be mixed in with the hemostatic and/or mucoadhesive liquids into liquid formulations.

In an alternative embodiment, a hemostatic composition and/or protective covering in the form of powders or granules can be reconstituted with a solvent or water or other liquid before use. Upon reconstitution, the formulations in the form of powders or granules can be mixed with dyes, colorants, flavorants, and/or other desired pharmaceutical ingredients, so the reconstituted solution can have pharmaceutical features of a liquid pharmaceutical.

In an alternative embodiment, protective coverings in the form of powders or granules can be reconstituted with a solvent or water or other liquid before use. Upon reconstitution, the formulations in the form of powders or granules can be mixed with dyes, colorants, flavorants, and/or other desired pharmaceutical ingredients, so the reconstituted solution can have pharmaceutical features of a liquid pharmaceutical.

Powders used for the purpose of formulations provided herein include formulations where a physician can use the formulation as is (i.e., in a powder form) or mix a directed amount of powder with a directed amount of a solvent or water or other liquid followed by localized administration at and about the site of the lesion with active bleeding and is capable of stopping the bleeding.

In certain embodiments, the protective covering may include multiple materials.

In one embodiment, the protective covering may include, e.g., an adhesive material (to adhere to the tissue) and a super-absorbent material (to act as a barrier to prevent liquids from contacting the lesion or blood from leaving the lesion site). Additionally or alternatively, the protective covering may include a hemostatic material (to coagulate blood in the event that the lesion bleeds) as one of its components. Additionally or alternatively, the protective covering may also include a pH modifying material, such as a base or an acid, or a buffer, in order to maintain adhesion in extreme pH or salinity environments.

For protective coverings that include acidic polymers (e.g., carbomers), elements that neutralize the polymers (achieving a pH range between 5-9) and thus increase viscosity include bases such as sodium hydroxide, ammonium hydroxide, potassium hydroxide, arginine, aminomethyl propanol, tetrahydroxypropyl ethylenediamine, triethanolamine, tromethamine, PEG-15 cocamine, diisopropanolamine, triisopropanolamine, and calcium carbonate. For protective coverings applied as gels or liquids the referenced bases may be dissolved with the protective covering before delivery. Likewise, protective coverings that are basic may include acidic elements to achieve a more neutral pH and thus increase adhesion. For protective coverings applied as powders the referenced pH modifiers may also be used in powder form and dissolved upon in-vivo hydration. To assist with manufacturing of protective coverings that contain pH modifying powders, it may be advantageous to avoid the use of hygroscopic powders and to use less absorbent powders such as calcium carbonate.

Figure 2:
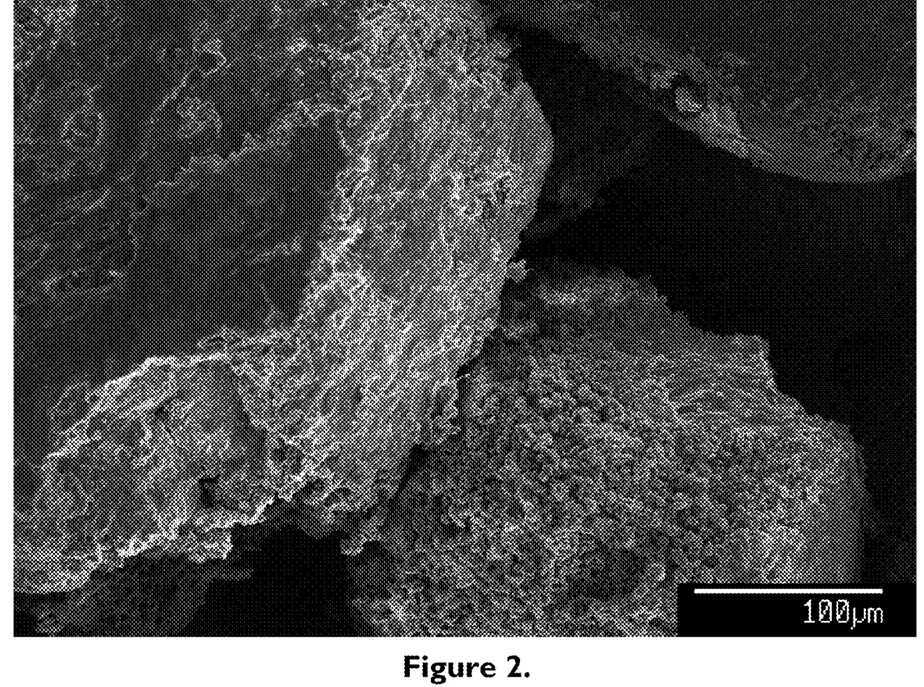
FIG. 2 is a photograph showing an example of a bound particles, where fine mucoadhesive particles are bound to larger barrier-forming particles.

For multi-component protective coverings delivered as powder, components may be bound together or consist of independent particles. Components that are bound together result in single particles that contain multiple elements. An example embodiment of bound particles could be fine mucoadhesive particles that are bound to larger barrier-forming particles (FIG. 2).

In yet another embodiment, an additive(s) to promote healing may be included in the protective covering.

Some examples of super-absorbent materials include absorbent clays (e.g., Laponite, Smectites, Zeolites), Diatomaceous Earth, and super-absorbent polymers (e.g., sodium polyacrylate, polyacrylamide copolymer, ethylene maleic anhydride copolymer, cross-linked carboxymethylcellulose, polyvinyl alcohol copolymers, cross-linked polyethylene oxide, and starch-acrylonitrile co-polymer).

In some embodiments, the protective covering may also include a hemostatic agent. The hemostatic agent may be the same or a different hemostatic agent as the hemostatic agent provided in the hemostatic composition. The protective covering may also include a combination of two or more hemostatic agents. Some examples of hemostatic agents include alginate, chitin, chitosan, collagen, fibrin, kaolinite clays, oxidized cellulose, plant-based polysaccharides, platelets, smectite clays, and zeolites.

Some examples of additives to promote healing include Aloe vera and derivatives, Honey and derivatives (i.e. Leptospermum scoparium honey), and Growth factors.

In certain embodiments, the protective covering may also include a mechanical scaffold to form a bandage, a patch, a dressing or the like. The term "scaffold" refers to any natural (e.g., extracellular matrix material or "ECM"), synthetic (e.g., woven or non-woven) material (e.g., Dacron™, electrospun materials and expanded PTFE) capable of providing a mechanical and structural support and strength to the protective covering.

The protective coverings may employ scaffolds, which may be applied in a variety of forms, including single- or multi-layer sheet or mesh constructs, fluidized formulations, and/or combinations thereof.

Examples of synthetic scaffolds include biocompatible materials, such as polyesters, such as polyethylene; poly (ethylene terephthalate); fluorinated polymers, such as polytetrafluoroethylene (PTFE) and fibers of expanded PTFE; polyurethanes; silicone, etc. One example of biocompatible polyester includes Dacron™ (DuPONT, Wilmington, Del.).

Examples of natural scaffold materials include bioremodelable ECM-based materials, such as naturally-derived collagenous ECM materials isolated from suitable animal or human tissue sources. As used herein, it is within the definition of a "naturally-derived ECM" to clean, delaminate, and/or comminute the ECM, or to cross-link the collagen or other components within the ECM. It is also within the definition of naturally occurring ECM to fully or partially remove one or more components or subcomponents of the naturally occurring matrix. Bioremodelable ECM materials possess biotropic properties capable of inducing tissue remodeling. Suitable ECM materials which can be processed to provide scaffold materials include, for example, submucosal (including for example small intestinal submucosa (SIS), stomach submucosa, urinary bladder submucosa, or uterine submucosa, each of these isolated from juvenile or adult animals), renal capsule membrane, dermal collagen, amnion, dura mater, pericardium, serosa, peritoneum or basement membrane layers or materials, including liver basement membrane or epithelial basement membrane materials, and others.

An exemplary ECM sheet material is a sheet of submucosa tissue graft material (OASIS™ Wound Matrix, Cook Biotech Incorporated, West Lafayette, Ind., USA).

A protective covering containing a scaffold and a mucoadhesive can be used in the treatment of a lesion in the gastrointestinal lesion. For these purposes, the scaffold material can be processed into the form of a sheet, bandage or other shape to occlude or cover at least partially the lesion site in the gastrointestinal tract.

In certain embodiments of the present invention, one or more adhesive (e.g., mucoadhesive) agents may be mixed with fluidized ECM material to form a substantially homogenous adhesive solution. The fluidized ECM material may be dried or formed into a gel for direct use.

In certain embodiments, comminuted submucosal or other ECM material can be dried by freeze drying to form a powder, which can hydrated, that is, combined with water or buffered saline and optionally other pharmaceutically acceptable excipients, to form a fluid ECM adhesive medical product. The viscosity of fluidized ECM compositions may be manipulated by controlling the concentration of the submucosa or other ECM components, the degree of hydration and adjusting the pH of the submucosal or other ECM digest. The viscosity may be adjusted to a range of about 2 to about 300,000 cps at 25° C. Higher viscosity gel formulations can have a gel or paste consistency and may be prepared by adjusting the pH of the digest solutions to about 6.0 to about 7.0.

Alternatively, the fluidized ECM material may be dried and adhered to or coated with the mucoadhesive agent(s).

In certain embodiments, the hemostatic composition is homogenous. The term "homogenous" means that the individual components of this layer are sufficiently distributed to behave as a single component. Likewise, in certain embodiments, the protective covering can be homogenous.

In certain embodiments, the protective covering can be a composite covering including additional layers such as biocompatible substrate films or layers. For example, the coverings may include a top sheet or impermeable layer to restrict passage of liquid, such as gastric acid back towards the lesion. Alternatively, or in addition, the covering may include an additional backing layer providing further barrier or structural support.

In certain embodiments, an adhesive may be incorporated into the scaffold by mixing, coating, spraying, impregnating the scaffold with the adhesive or may be provided as a separate adhesive layer forming an adhesive-coated margin. Certain preparation techniques, such as lyophilizing, critical point drying, or use of low surface tension solvents (e.g. ethyl acetate, alcohol, benzene) can be used to maintain the adhesive properties during the incorporation process.

In certain embodiments, the protective covering may include a mucoadhesive covering on the interface that is placed on the gastrointestinal tissue and an additional material such as a woven mesh scaffold on the lumen interface to provide improved mechanical strength to the covering.

In certain embodiments, the hemostatic composition and/or the protective covering disclosed herein and used herein may comprise one or more excipients. Specifically, additional excipients useful herein include, by way of non-limiting example, solvents, binders, fillers, lubricants, suspension agents, flavoring agents, color indicators (e.g., dyes), sweeteners, preservatives, antioxidants, buffering agents, humectants, chelating agents, surfactants, disintegrating agents, crosslinking agents, and the like. These excipients can extend the time the hemostatic composition and/or protective covering is in contact with a lesion site in the gastrointestinal tract and/or can increase the interaction of the hemostatic composition and/or protective covering with a gastrointestinal surface, such as viscosity enhancing agents or absorption enhancing agents may be used.

In certain embodiments, the hemostatic composition and/or the protective covering include a solvent. Exemplary solvents include ethyl acetate, ethyl alcohol, water, DMSO, saline, acetone, isopropyl alcohol, or a combination thereof. If a solvent is used, the resultant components are in the form of a liquid or a gel and may be delivered as such to the site of the lesion with active bleeding.

Optionally, the hemostatic composition and/or the protective covering may include one or more binder, optionally one or more filler, optionally one or more lubricant, optionally one or more suspension agent, optionally one or more flavoring agent, optionally one or more coloring agent, optionally one or more sweetener, optionally one or more preservative, optionally one or more antioxidant, optionally one or more buffering agent, optionally one or more humectant, optionally one or more chelating agent, optionally one or more disintegrating agent, and optionally one or more surfactant.

In addition, the hemostatic composition and/or the protective covering may include, for example, a color indicator, such as a dye that upon the application to and about the lesion site changes color. Water soluble dyes are preferable. Exemplary dyes include indigo carmine, methylene blue, fluorescent proteins, Rose Bengal, India ink, and others.

Preservatives include, for example, benzalkonium chloride, cetrimide (cetyltrimethylammonium bromide), benzoic acid, benzyl alcohol, methyl-, ethyl-, propyl- and butyl-esters of para-hydroxybenzoic acid, chlorhexidine, chlorobutanol, phenylmercuric acetate, borate and nitrate, potassium sorbate, sodium benzoate, sorbic acid, thiomersal (mercurithiosalicylate), combinations thereof, or the like.

Antioxidants include, for example, ascorbyl palmitate, butylated hydroxyanisole, butylated hydroxytoluene, monothioglycerol, sodium ascorbate, sodium formaldehyde sulfoxylate, sodium metabisulfite, BHT, BHA, sodium bisulfite, vitamin E or a derivative thereof, propyl gallate, edetate (EDTA) (e.g., disodium edetate), Diethylenetriaminepentaacetic acid (DTPA), Triglycollamate (NT), combinations thereof, or the like.

Additionally, in certain embodiments, buffering agents, humectants, or chelating agents may also be incorporated into the hemostatic composition and/or the protective covering.

Exemplary buffering agents include citrate buffers (i.e., citric acid and citrate), phosphate buffers, acetate buffers, carbonate buffers (e.g., calcium carbonate, sodium bicarbonate, or the like), hydroxide (e.g., magnesium hydroxide, sodium hydroxide, or the like), combinations thereof, or the like.

Humectants include, for example, glycerine, propylene glycol, ethylene glycol, glyceryl triacetate, polyols (e.g., sorbitol, xylitol, maltitol, polydextrose), and the like.

Chelating agents include, for example, edetate (EDTA) (e.g., disodium edetate), Diethylenetriaminepentaacetic acid (DTPA), Triglycollamate (NT), or the like.

In some embodiments, the hemostatic composition and/or the protective covering may further include at least one therapeutic agent. Exemplary therapeutic agents that may be incorporated into the hemostatic composition and/or the protective covering include antibiotics, antiseptic agents, proton pump inhibitors, matrix metalloproteinases, or tissue growth promoting compounds.

Other therapeutic agents may also be included and would be known to a skilled artisan.

A contrast agent may be used in conjunction with the injection of the hemostatic composition and protective covering. The contrast agent may be injected prior to injection of the two materials. Alternatively, the contrast agent is included in the hemostatic component or protective covering component that is injected at and about the site of a lesion with an active bleeding in the gastrointestinal tract. Contrast agents and their use are well known to one of skill in the art.

In certain embodiments, a composition comprising a hemostatic agent may be delivered to and about the site of the lesion with active bleeding for purposes of hemostasis and before a protective covering including an adhesive agent is delivered.

For example, if used for purposes of hemostasis, thrombin, epinephrine, hemostatic powders, or a sclerosant may be provided to reduce localized bleeding at the lesion site. In addition to the hemostatic properties of the hemostatic agent, it should be noted that the relatively high pressure of the fluid and therapeutic agent, by itself, may act as a mechanical tamponade by providing a compressive force, thereby reducing the time needed to achieve hemostasis.

As noted above, the hemostatic compositions may be delivered in any suitable form. For example, the hemostatic composition may comprise a powder, liquid, gel, aerosol, or other substance.

In certain embodiments, the protective coverings are prepared for a local and direct delivery at and about a site of a lesion, where the protective covering upon the delivery or application to the lesion forms a coating or a patch or the like over the applied hemostatic composition at and about the site of the lesion and is capable of remaining at and about the site of the lesion for a time sufficient to allow the site to be treated or healed. Preferably, at least partial coverage of the lesion site is achieved; most preferably a complete coverage of the lesion site is achieved. The time sufficient to allow the site to be treated or healed may vary depending on the location, type and size of the lesion and may be anywhere from 30 minutes (sufficient to stop bleeding) to 72 hours or more (sufficient to allow the tissue to heal almost completely). Preferably, the time sufficient to allow the site to be treated or healed is at least 1 hour; more preferably the time sufficient to allow the site to be treated or healed is at least 3 hours; more preferably the time sufficient to allow the site to be treated or healed is at least 6 hours; more preferably the time sufficient to allow the site to be treated or healed is at least 10 hours; more preferably the time sufficient to allow the site to be treated or healed is at least 12 hours; more preferably the time sufficient to allow the site to be treated or healed is at least 18 hours; more preferably the time sufficient to allow the site to be treated or healed is at least 24 hours; more preferably the time sufficient to allow the site to be treated or healed is at least 36 hours; more preferably the time sufficient to allow the site to be treated or healed is at least 48 hours; more preferably the time sufficient to allow the site to be treated or healed is at least 72 hours; most preferably the time sufficient to allow the site to be treated or healed is 48-72 hours.

Methods and Delivery

Certain embodiments relate to a method for protecting or treating a lesion with an active bleeding in the gastrointestinal tract. The method includes directly applying a composition comprising a hemostatic agent at and about a site of the lesion in the gastrointestinal tract to stop the active bleeding; and once the active bleeding is stopped, directly applying a protective covering comprising an adhesive agent over and about at least a portion of the previously applied composition comprising the hemostatic agent at and about the lesion site in the gastrointestinal tract. The protective covering upon application over and about at least a portion of hemostatic composition at and about the site of the lesion adheres to and is in direct contact with both, the hemostatic composition/layer and the surrounding gastrointestinal tissue, provides a sustained protective barrier, and is capable of remaining at and about the site of the lesion for a minimum of 30 minutes.

In certain embodiments, the hemostatic composition and the protective covering can be applied or delivered to and about the site of the lesion with active bleeding through endoscopic techniques, laparoscopic techniques, or through direct access (i.e., surgically) using, for example any suitable catheter delivery system.

In certain embodiments, the hemostatic composition and the protective covering may be delivered via an intraluminal delivery system. The hemostatic composition and the protective covering may be applied via spraying, ejecting, injecting, or spreading.

An advantage of this bimodal treatment is that the delivery of the hemostatic composition and the protective covering is during the same procedure, which can minimize and/or eliminate repeat procedures.

In certain embodiments, the hemostatic composition and the protective covering may be through a multi-lumen catheter.

Specifically, the delivery system may include a delivery device that is sized and configured to deliver and apply the hemostatic composition and the protective covering directly at a targeted tissue region within a body lumen or hollow body organ, i.e., such as the site of the lesion, e.g., a lesion with an active bleeding in the gastrointestinal tract.

Also, the delivery device can be sized and configured to accommodate passage over a guide wire. In this way, the device can be introduced over the guide wire under direct visualization from an endoscope. Specifically, the guide wire can run next to the endoscope and therefore leaves a working channel of the endoscope free. In an alternative embodiment, the delivery device can be sized and configured to be back-loaded through the working channel of the endoscope. The working channel of the endoscope thereby serves to guide the delivery device while providing direct visualization.

Various delivery systems for localized delivery of therapeutic agents are known and may be used to deliver the two components described herein.

In certain embodiments, the delivery of the hemostatic composition and the protective covering may be via, e.g., a system suitable for delivering therapeutic agents to a target site. An exemplary system has been previously described in U.S. Pat. Pub. No. 2015/0094649, which is incorporated herein in its entirety.

In certain embodiments, the delivery of the hemostatic composition and the protective covering may be via, e.g., a "two-barrel" device. An exemplary two-barrel device has been previously described in U.S. Pat. Pub. No. 2008/0060970, which is incorporated herein in its entirety.

In short, an exemplary two-barrel device may include a cartridge having at least two cylinder bores for delivery of the hemostatic agent and the protective covering, wherein each cylinder includes an exit port for the hemostatic agent and the protective covering, a plunger within each cylinder for pushing the materials out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

An alternative delivery system may be one described in U.S. Pat. Pub. No. 2002/0170926, which is incorporated herein in its entirety.

In certain embodiments, the step of applying the hemostatic composition may include inserting a first delivery device, such as a syringe loaded with the hemostatic composition at and about the site of the lesion with the active bleeding and applying the hemostatic composition at and over the lesion with the active bleeding to stop the active bleeding. Applying may be via spraying, ejecting or spreading the hemostatic composition at and about the site of the lesion with the active bleeding.

In certain embodiments, the step of applying the protective covering may include inserting a second delivery device, such as a syringe loaded with the protective covering at and about the site of the lesion with the active bleeding and applying the protective covering on top of and about at least a portion of hemostatic composition. Applying may be via spraying, ejecting or spreading the protective covering on top of and about at least a portion of the previously applied hemostatic composition at and about the lesion site in the gastrointestinal tract.

Certain other embodiments relate to a method for protecting or treating a lesion in the gastrointestinal tract arising from the disorders of the gastrointestinal tract and or medical procedures that require removal of the mucosal or submucosal layers of gastrointestinal tract wall, the lesion actively bleeding. The lesion may be a post-mucosectomy lesion.

The method includes locally applying a hemostatic composition and an adhesive protective covering to and about the lesion in the gastrointestinal tract. Upon the application of the two components, the product forms a protective coating or covering at the site of the lesion, where the coating is capable of remaining at and about the site of the lesion for at least 30 minutes, more preferably 24-72 hours or longer.

In certain embodiments, both components may be applied in a powder form. Alternatively, the components may be applied in a liquid or gel form. The types of hemostatic compositions and protective covering products and formulations suitable for use in the methods of this invention were described in detail above.

In certain embodiments, the step of applying the adhesive medical product comprises inserting a syringe loaded with the protective covering about the site of the lesion and applying the covering at and about the site of the lesion by spraying, injecting, ejecting or spreading the composition directly at and about the site of the lesion so as to provide at least partial but more preferably a complete coverage of the lesion. As previously discussed in connection with the delivery methods, the applying may be through endoscopic, laparoscopic techniques or direct access (i.e., surgically) using a catheter-based delivery system (single lumen or multi-lumen catheter system).

In certain embodiments, a crosslinking initiator, such as chemical, thermal, light, curing agent or a catalyst may be used to aid in the process of solidifying of the coating at and about the lesion site. The crosslinking initiator may interact homogenously or heterogeneously with the coating and may be applied to the coating before, after, or during the coating delivery. Without being bound by the theory, upon the application of hemostatic composition to a lesion with active bleeding, the bleeding will stop. Upon the application of the protective covering on top of and about the hemostatic composition and the lesion site, the covering will remain at and about the site of the lesion for the time sufficient for the lesion to heal (anywhere from 30 minutes to 72 hours or longer). Once the lesion is healed, the covering will either get washed off or erode over time; the covering will then be passed through the digestive system for removal from the body. Alternatively, the covering will remain at the site of the lesion until the outer most mucosal layer sloughs off of sheds during a normal biological process over 2-3 weeks and the coating or covering comes off with the mucosal layer.

Use

The medical products described herein can find wide use in the field of medicine, and in this regard, can be adapted to provide a variety of devices and objects suitable for application to and/or implantation within a patient, and especially in the gastrointestinal tract. The present invention also provides, in certain aspects, various methods for using these materials, for example, to replace, augment, repair, and/or otherwise suitably treat diseased or otherwise damaged or defective gastrointestinal tissue of a patient.

Illustratively, medical products of the invention can be configured as medical products suitable for healing tissue, providing hemostasis, and/or providing occlusion within the body of a patient (e.g., bandage, dressing, patch, etc.).

In some embodiments, the adhesive medical products of the present invention are configured as single- or multilayered patches or other sheet or sheet-like devices for providing support to patient tissue or otherwise treating patient's gastrointestinal tissue.

Specifically, the long-lasting adhesive medical products of the present invention may be used to protect, treat or heal a lesion site in the gastrointestinal tract. Specifically, the present adhesive medical products may be used to treat a lesion arising from the disorders of the gastrointestinal tract and or medical procedures that require removal of the mucosal or submucosal layers of gastrointestinal tract wall, such as endoscopic submucosal dissection, endoscopic mucosal resection, polypectomy, ulcer, cancer, varices, Barrett's esophagus ablation, a combination thereof, or others.

Illustratively, medical products of the present invention can be processed into various shapes and configurations, for example, a sheet form, which may be used as a bandage, patch, coating, etc.

In additional embodiments, the medical product of the present invention may be used for closing a perforation, anastomosis, or fistula of the gastrointestinal tract. The medical product comprises a protecting covering as discussed above, wherein upon the application of the medical product, the protective covering forms a seal over the perforation, anastomosis, or fistula. The medical product may be used in combination with other medical products, such as clips or sutures.

The following examples are included to demonstrate certain embodiments of the invention. Those of skill in the art should, however, in light of the present disclosure, appreciate that modifications can be made in the specific embodiments that are disclosed and still obtain a like or similar result without departing from the spirit and scope of the invention. Therefore, the examples are to be interpreted as illustrative and not in a limiting sense.

EXAMPLES

Example 1

Liquid Mucoadhesive Benchtop Testing

Various solutions of Carbopol™ were tested: (1) Carbopol™ dissolved in ethyl acetate, (2) Carbopol™ dissolved in ethyl alcohol, and (3) Carbopol™ dissolved in water. The Carbopol™ solutions were applied to excised stomach and intestinal tissue.

Figure 1:
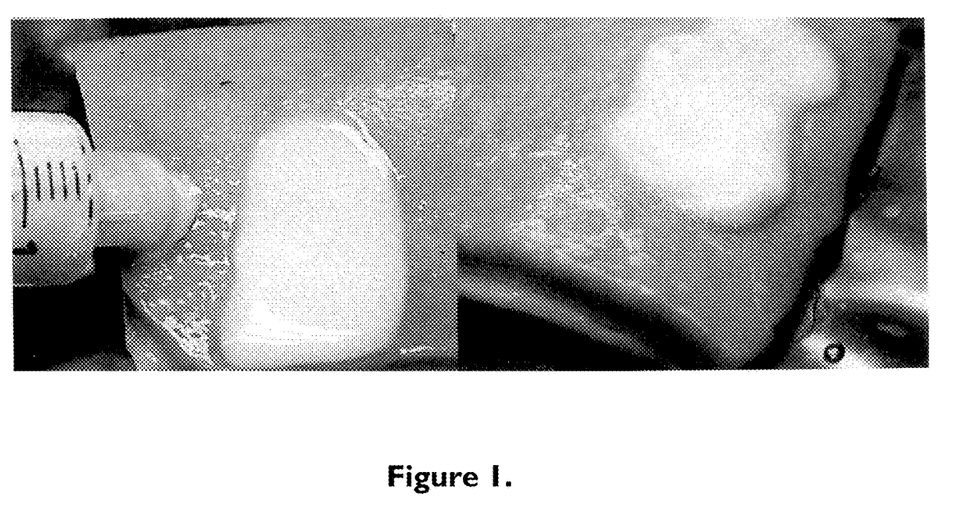
FIG. 1 is a photograph showing an example of a mucoadhesive covering of the present invention.

Specifically, all three solutions of Carbopol™ were loaded into a syringe and injected directly at the lesion site through a catheter. Ethyl acetate (as shown in FIG. 1) was found to be a most suitable solvent to allow the highest concentration of Carbopol™. The next best was ethyl alcohol followed by water which was necessary to be highly dilute.

Next, the dye indigo carmine was mixed with the ethyl alcohol solvent. This solution remained white, with small blue particles of the dye suspended in it. However, upon application to the tissue the suspension turned blue as water from the tissue became absorbed into the adhesive. This suggests that use of a dye may be suitable for visualization of the lesion site that is being treated.

Example 2

Bi-Modal Animal Survival Testing

Figure 3:
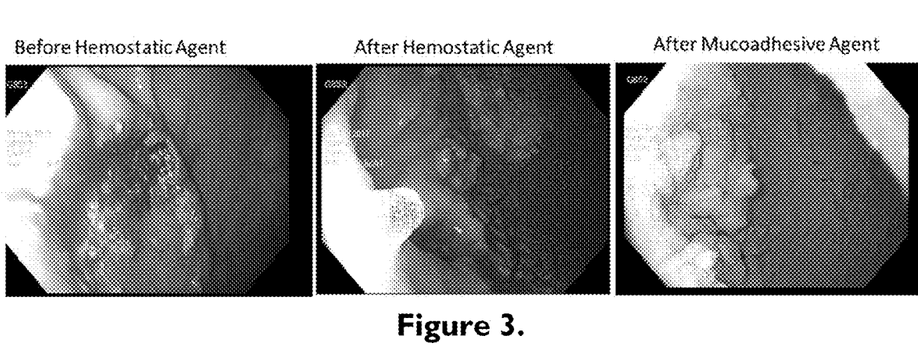
FIG. 3 shows photographs of active gastrointestinal bleeding in pigs that were treated with Hemospray™ powder and a mucoadhesive powder sprayed on top as a protective covering.
Figure 4:
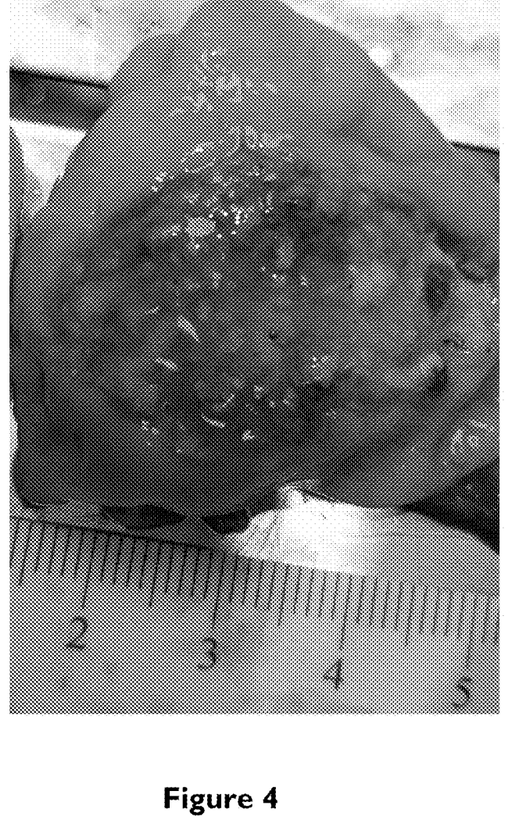
FIG. 4 shows a photograph of an endoscopic submucosal resection at 72 hours. At time of lesion creation the lesion had an active bleed and was treated with a bimodal application of Hemospray™ and a protective mucoadhesive. At 72 hours, the presence of the protective mucoadhesive covering and relatively less gross inflammation can be seen when compared to a lesion that did not undergo bimodal treatment (FIG. 5).
Figure 5:
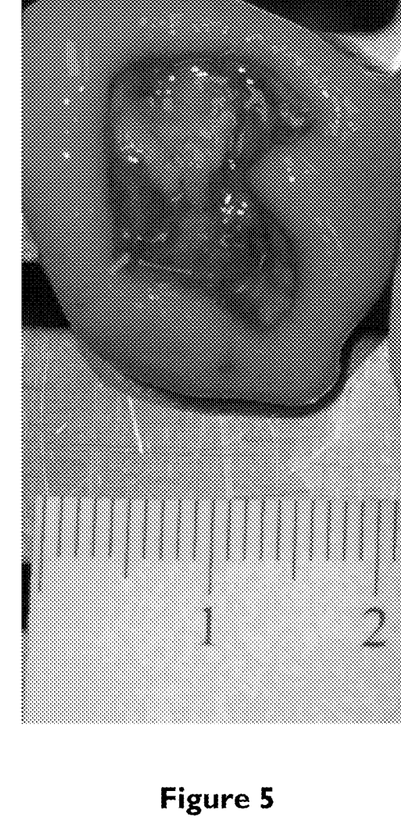
FIG. 5 shows a photograph of an endoscopic submucosal resection at 72 hours. At time of lesion creation the lesion had an active bleed and was treated with Hemospray™. No protective mucoadhesive was applied. At 72 hours, there is no presence of a protective covering and increased gross inflammation (redness) can be observed when compared to a lesion that underwent bimodal treatment (FIG. 4).

To determine the sustainability and protective effects of a coating on top of a hemostatic treatment, active gastrointestinal bleeding in pigs were treated with Hemospray™ powder, and a mucoadhesive powder (comprised of Carbopol mucoadhesive, smectite clay as a barrier, and calcium carbonate as a pH modifier) was sprayed on top as a protective covering. FIG. 3 shows a gastrointestinal bleed before and after acute treatment with Hemospray™ powder followed by an application of a mucoadhesive powder (FIG. 4 shows a 72 hour time point). Control sites were treated with only Hemospray™ powder (FIG. 5 shows a 72 hour time point.)

To increase the likelihood of recurrent bleeding occurring, the pigs were given an antiplatelet medication (rivaroxaban) post-procedure. Hemoglobin values were measured at 0, 12, 24, 36, 48, 60, and 72 hours to quantify blood loss.

The animals treated with Hemospray alone had an average net Hemoglobin drop (a measure of total blood loss) of 6.6 g/dL versus 3.35 d/gL for the animals that had a protective covering on top of the Hemospray over the 72 hour time period. Referring to FIG. 4, adherent material could still be seen on the sites that contained the protective covering, but not on the sites treated with Hemospray alone (FIG. 5).

The invention claimed is:

1. A system for achieving hemostasis of an actively bleeding lesion and maintaining hemostasis of said lesion, comprising:
    (i) at least one pressure source;
    (ii) at least one catheter;
    (iii) a hemostatic powder in a container, the container adapted to be in fluid communication with the at least one pressure source and the at least one catheter; and
    (iv) an adhesive powder;
    wherein the at least one pressure source is capable of propelling the hemostatic powder first to flow through the catheter to and about the site of the actively bleeding lesion, wherein upon delivery of the hemostatic powder to and about the site of the lesion, a hemostatic layer is formed at and about the site of the lesion, at least partially or completely covering the lesion;
    wherein the catheter of the system comprises a multi-lumen catheter, where the hemostatic powder and the adhesive powder are delivered through the multi-lumen catheter;
    wherein the system is configured to withhold the adhesive powder from initial delivery to the lesion until the active bleeding has been stopped or slowed by the hemostatic powder, and after the active bleeding has been stopped or slowed by the hemostatic powder, the adhesive powder is capable of being separately delivered to flow on top, over and/or about at least a portion of the hemostatic layer, wherein upon delivery of the adhesive powder, a protective covering is formed at least partially or completely covering the hemostatic layer and surrounding tissue; and
    wherein, the hemostatic layer and the protective covering are capable of remaining at and about a site of the lesion for a minimum of 30 minutes.

2. The system of claim 1, wherein the lesion is a mucosal lesion.

3. The system of claim 1, wherein the adhesive powder comprises a mucoadhesive agent.

4. The system of claim 1, wherein the hemostatic layer and the protective covering together are a minimum of 0.1 mm in thickness.

5. The system of claim 1, wherein the hemostatic powder comprises a hemostatic clay.

6. The system of claim 1, further comprising a pH modifier.

7. The system of claim 1, wherein the hemostatic layer and the protective covering are capable of remaining at and about the site of the lesion for a minimum of 48 hours.

8. The system of claim 1, wherein the hemostatic layer and the protective covering are capable of remaining at and about the site of the lesion for a minimum of 72 hours.

9. The system of claim 1, wherein the adhesive powder is in a form of particles comprised of adhesive particles and barrier forming particles that are bound together.

10. The system of claim 1, further comprising: (v) instructions for a medical practitioner to apply the adhesive powder on top, over and/or about at least a portion of the hemostatic layer at and about the site of the actively bleeding lesion.

11. A system for achieving hemostasis of an actively bleeding lesion and maintaining hemostasis of said lesion, comprising:
    a hemostatic layer, comprising a hemostatic agent in the form of a liquid, gel, or powder;
    a protective covering, comprising an adhesive agent in the form a liquid, gel, or powder;
    wherein the system comprises one of: i) a multi-lumen catheter, where the hemostatic agent and the adhesive agent are delivered through the multi-lumen catheter; or ii) a first delivery device comprising a syringe loaded with the hemostatic agent, and a second delivery device comprising a syringe loaded with the adhesive agent,
    wherein the second delivery device is actuatable after the first delivery device,
    wherein the system is configured to withhold the adhesive agent from initial delivery to the lesion until the active bleeding has been stopped or slowed by the hemostatic agent, such that the hemostatic agent is initially in direct contact with the actively bleeding lesion, and the adhesive agent is subsequently in direct contact with both the hemostatic layer and surrounding tissue,
    wherein the protective covering is capable of remaining at and about a site of the lesion for a minimum of 30 minutes, and
    wherein the protective covering comprises multiple components that, in addition to the adhesive agent, also includes a buffer.

12. The system of claim 11, wherein the protective covering further includes a colorant or dye.

13. The system of claim 11, wherein the hemostatic agent comprises chitosan.

14. The system of claim 13, wherein the protective covering further includes a colorant or dye.

15. A system for achieving hemostasis of an actively bleeding lesion and maintaining hemostasis of said lesion, comprising:
    a hemostatic powder;
    an adhesive powder;
    a first delivery device comprising a syringe loaded with the hemostatic powder; and
    a second delivery device comprising a syringe loaded with the adhesive powder, wherein the second delivery device is actuatable after the first delivery device,
    wherein the first delivery device is capable of delivering the hemostatic powder first to flow to and about the site of the actively bleeding lesion, wherein upon delivery of the hemostatic powder to and about the site of the lesion, a hemostatic layer is formed at and about the site of the lesion, at least partially or completely covering the lesion;
    wherein the system is configured to withhold the adhesive powder from initial delivery to the lesion until the active bleeding has been stopped or slowed by the hemostatic powder, and after the active bleeding has been stopped or slowed by the hemostatic powder, the adhesive powder is capable of being separately delivered by the second delivery device to flow on top, over and/or about at least a portion of the hemostatic layer, wherein upon delivery of the adhesive powder, a protective covering is formed at least partially or completely covering the hemostatic layer and the surrounding tissue;

wherein, the hemostatic layer and the protective covering are capable of remaining at and about a site of the lesion for a minimum of 30 minutes.

* * * * *